(12) United States Patent
Collins et al.

(10) Patent No.: US 9,821,046 B2
(45) Date of Patent: Nov. 21, 2017

(54) COMPOSITION AND USES THEREOF

(71) Applicant: OXFORD UNIVERSITY INNOVATION LIMITED, Oxford (GB)

(72) Inventors: Katharine Alice Collins, Oxford (GB); Sarah Catharine Gilbert, Oxford (GB); Adrian Vivian Sinton Hill, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 14/762,106

(22) PCT Filed: Jan. 21, 2014

(86) PCT No.: PCT/GB2014/050156
§ 371 (c)(1),
(2) Date: Jul. 20, 2015

(87) PCT Pub. No.: WO2014/111733
PCT Pub. Date: Jul. 24, 2014

(65) Prior Publication Data
US 2016/0144011 A1 May 26, 2016

(30) Foreign Application Priority Data

Jan. 21, 2013 (GB) .................................. 1301022.8
May 8, 2013 (GB) .................................. 1308242.5

(51) Int. Cl.
| | | |
|---|---|---|
| *A61K 39/15* | (2006.01) | |
| *C07K 14/445* | (2006.01) | |
| *A61K 39/015* | (2006.01) | |
| *A61K 39/12* | (2006.01) | |
| *A61K 38/16* | (2006.01) | |
| *C07K 16/08* | (2006.01) | |
| *C07K 16/20* | (2006.01) | |
| *C12N 7/00* | (2006.01) | |
| *A61K 39/00* | (2006.01) | |

(52) U.S. Cl.
CPC .......... *A61K 39/015* (2013.01); *A61K 38/162* (2013.01); *A61K 39/12* (2013.01); *C07K 14/445* (2013.01); *C07K 16/082* (2013.01); *C07K 16/205* (2013.01); *C12N 7/00* (2013.01); *A61K 2039/522* (2013.01); *A61K 2039/523* (2013.01); *A61K 2039/5256* (2013.01); *A61K 2039/55516* (2013.01); *A61K 2039/55555* (2013.01); *A61K 2039/55577* (2013.01); *A61K 2039/70* (2013.01); *C07K 2319/00* (2013.01); *C07K 2319/40* (2013.01); *C12N 2710/10041* (2013.01); *C12N 2710/24121* (2013.01); *C12N 2710/24134* (2013.01); *C12N 2710/24141* (2013.01); *C12N 2710/24143* (2013.01); *C12N 2710/24171* (2013.01); *C12N 2730/10134* (2013.01); *C12N 2730/10171* (2013.01)

(58) Field of Classification Search
None
See application file for complete search history.

(56) References Cited

FOREIGN PATENT DOCUMENTS

| | | |
|---|---|---|
| WO | 93/10152 A1 | 5/1993 |
| WO | 2004/110482 A1 | 12/2004 |
| WO | 2008/009650 A2 | 1/2008 |

OTHER PUBLICATIONS

Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Rutgers et al., "Hepatitis B surface antigen as carrier matrix for the repetitive epitope of the circumsporozoite protein of Plasmodium falciparum," Biotechnology, 6(9):1065-70 (1988).
Vreden et al., "Phase I clinical trial of a recombinant malaria vaccine consisting of the circumsporozoite repeat region of Plasmodium falciparum coupled to hepatitis B surface antigen," Am J Trop Med Hyg., 45(5):533-8 (1991).
Gordon et al., "Safety, immunogenicity, and efficacy of a recombinantly produced Plasmodium falciparum circumsporozoite protein-hepatitis B surface antigen subunit vaccine," J Infect Dis. 171(6):1576-85 (1995).
Dunachie et al., "A clinical trial of prime-boost immunisation with the candidate malaria vaccines RTS, S/AS02A and MVA-CS," Vaccine, 24(15):2850-9 (2006).
Hutchings et al., "Combination of protein and viral vaccines induces potent cellular and humoral immune responses and enhanced protection from murine malaria challenge," Infect Immunity, 75(12):5819-26 (2007).
Lee et al., "Presentation of the hydrophilic domains of hepatitis C viral E2 envelope glycoprotein on hepatitis B surface antigen particles," J Med Virol., 50(2):145-51 (1996).
Stoute et al., "A preliminary evaluation of a recombinant circumsporozoite protein vaccine against Plasmodium falciparum malaria," N Engl J Med., 336(2):86-91 (1997).
Lalvani et al., "Potent induction of focused Th1-type cellular and humoral immune responses by RTS,S/SBAS2, a recombinant Plasmodium falciparum malaria vaccine," J Infect Dis., 180(5):1656-64 (1999).

* cited by examiner

*Primary Examiner* — Jennifer Graser
(74) *Attorney, Agent, or Firm* — Nixon Peabody LLP; Mark J. FitzGerald; Teresa A. Ptashka

(57) ABSTRACT

The present invention provides a particle comprising a fusion protein, wherein the fusion protein comprises at least one NANP repeat (SEQ ID NO: 7), some or all of the C-terminus of the CS protein from *Plasmodium falciparum* and a hepatitis B surface antigen, and wherein the particle comprises no, or substantially no, free hepatitis B surface antigen protein, and uses thereof.

8 Claims, 15 Drawing Sheets

Figure 2B:
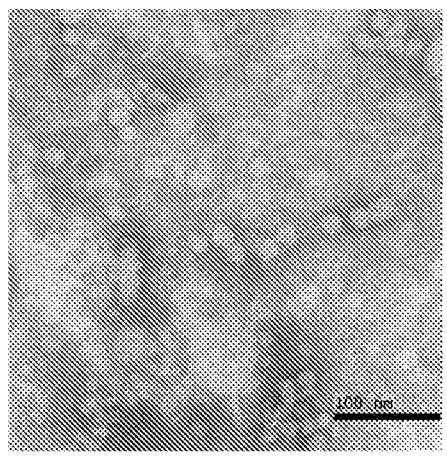

Seq ID No: 1
MDPNANPNANPNANPNANPNANPNANPNANPNANPNANPNANPNANPNAN
PNANPNANPNANPNANPNANPNANPNKNNQGNGQGHNMPNDPNRNVDEN
ANANSAVKNNNNEEPSDKHIKEYLNKIQNSLSTEWSPCSVTCGNGIQVRIKPG
SANKPKDELDYANDIEKKICKMEKCSSVPVTNMENITSGFLGPLLVLQAGFFLL
TRILTIPQSLDSWWTSLNFLGGSPVCLGQNSQSPTSNHSPTSCPPICPGYRW
MCLRRFIIFLFILLLCLIFLLVLLDYQGMLPVCPLIPGSTTTNTGPCKTCTTPAQG
NSMFPSCCCTKPTDGNCTCIPIPSSWAFAKYLWEWASVRFSWLSLLVPFVQW
FVGLSPTVWLSAIWMMWYWGPSLYSIVSPFIPLLPIFFCLWVYI

Seq ID No: 2
MMAPDPNANPNANPNANPNANPNANPNANPNANPNANPNANPNANPNANP
NANPNANPNANPNANPNANPNANPNANPNKNNQGNGQGHNMPNDPNRNV
DENANANSAVKNNNNEEPSDKHIKEYLNKIQNSLSTEWSPCSVTCGNGIQVRI
KPGSANKPKDELDYANDIEKKICKMEKCSSVFNVVNSSIGLGPVTNMENITSGF
LGPLLVLQAGFFLLTRILTIPQSLDSWWTSLNFLGGSPVCLGQNSQSPTSNHS
PTSCPPICPGYRWMCLRRFIIFLFILLLCLIFLLVLLDYQGMLPVCPLIPGSTTTN
TGPCKTCTTPAQGNSMFPSCCCTKPTDGNCTCIPIPSSWAFAKYLWEWASVR
FSWLSLLVPFVQWFVGLSPTVWLSAIWMMWYWGPSLYSIVSPFIPLLPIFFCL
WVYI

Figure 1

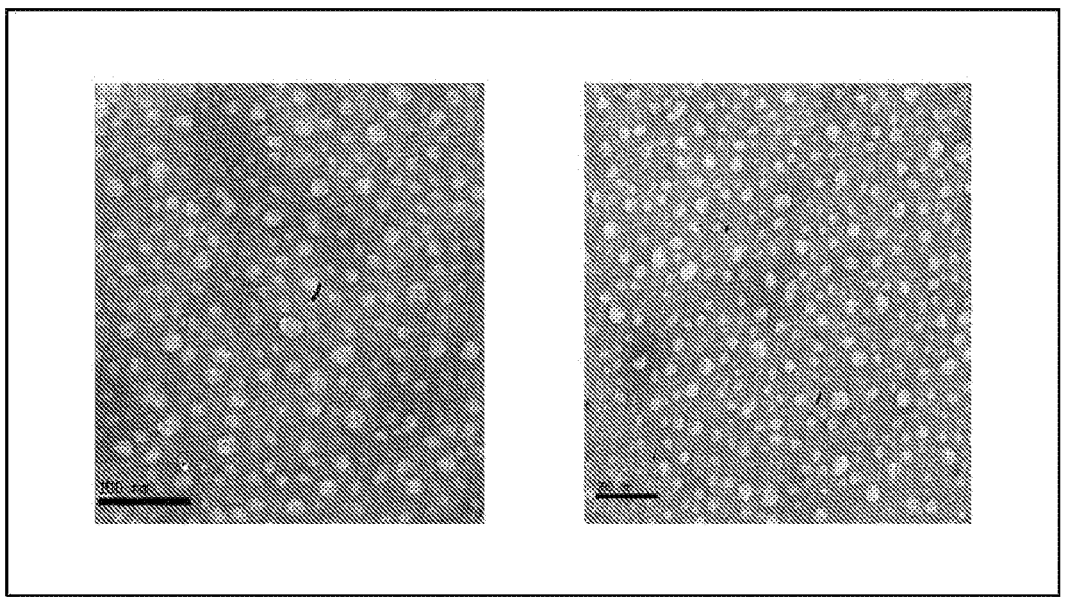

Figure 2A

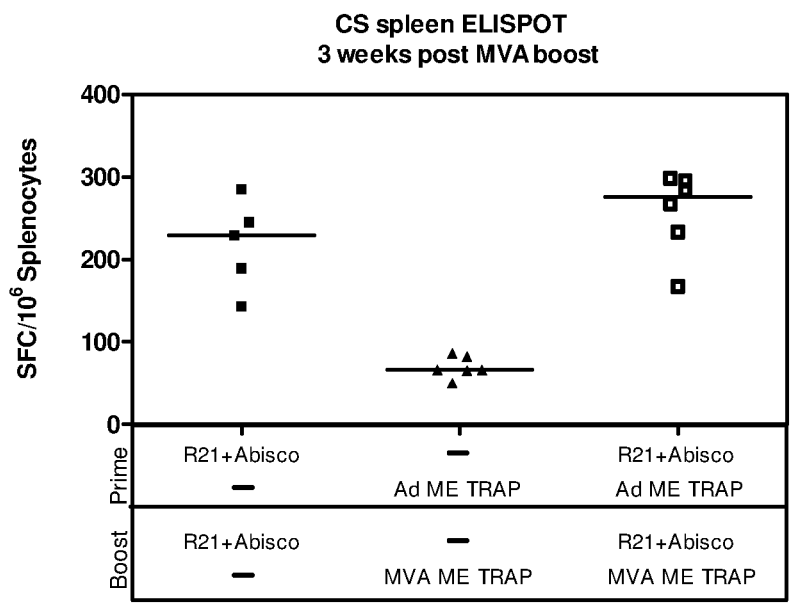
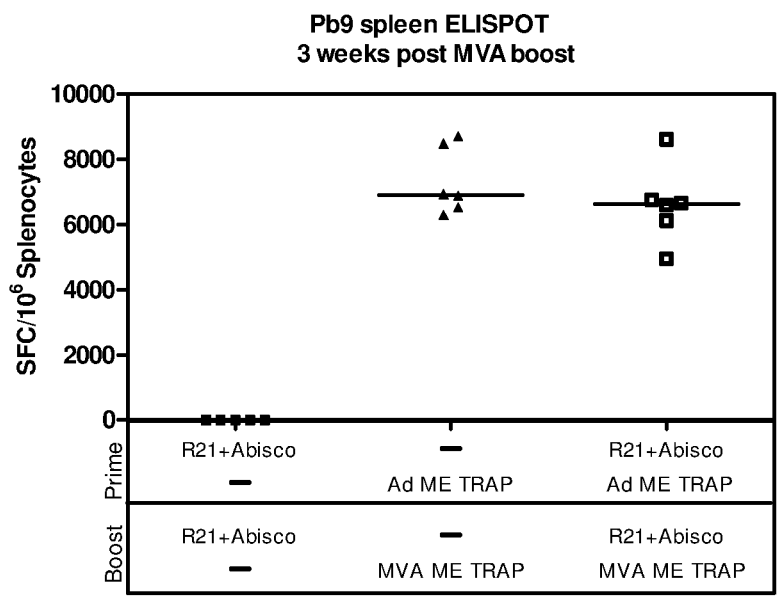
Figure 8

| Group | No. of mice | Prime | Boost | Interval |
|---|---|---|---|---|
| 1 | 8 | R21 + Abisco IM | R21 + Abisco IM | 8 weeks |
| 2 | 8 | R21 + Matrix M IM | R21 + Matrix M IM | 8 weeks |
| 3 | 8 | ChAd63 CS IM | MVA CS IM | 8 weeks |
| 4 | 10 | Adjuvant only | Adjuvant only | 8 weeks |

| Gp | No. mice | Vaccine | No. shots | Interval |
|---|---|---|---|---|
| 1 | 6 | 0.5µg R21 IM (no adjuvant) | 3 | 3 weeks |
| 2 | 6 | 0.5µg R21 + Alhydrogel IM | 3 | 3 weeks |
| 3 | 6 | 0.5µg R21 + Abisco IM | 3 | 3 weeks |

| Gp | No. mice | Vaccine | No. shots | Interval |
|---|---|---|---|---|
| 1 | 6 | 0.5µg R21 + Abisco IM | 3 | 3 weeks |
| 2 | 6 | 0.5µg R21 + Abisco IM | 3 | 4 weeks |
| 3 | 6 | 0.5µg R21 + Abisco IM | 2 | 8 weeks |
| 4 | 6 | 0.5µg R21 + Abisco IM | 3 | 8 weeks |

| Gp | No. mice | Vaccine | No. shots | Interval |
|---|---|---|---|---|
| 1 | 6 | 0.5μg R21 Matrix M IM | 2 | 8 weeks |
| 2 | 6 | 0.5μg R21 + MF59 IM | 2 | 8 weeks |
| 3 | 6 | 0.5μg R21 + L-AS01 IM | 2 | 8 weeks |
| 4 | 6 | 0.5μg CSP Matrix M IM | 2 | 8 weeks |
| 5 | 6 | 0.5μg CSP + MF59 IM | 2 | 8 weeks |
| 6 | 6 | 0.5μg CSP + L-AS01 IM | 2 | 8 weeks |

COMPOSITION AND USES THEREOF

CROSS-REFERENCE TO RELATED APPLICATIONS

This application is a 35 U.S.C. §371 National Phase Entry Application of International Application No. PCT/GB2014/050156 filed Jan. 21, 2014, which designates the U.S., and which claims the benefit of GB Application No. 1308242.5, filed May 8, 2013, and the benefit of GB Application No. 1301022.8, filed Jan. 21, 2013, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 20, 2015 is named 20151022_Sequence_Listing_052342-085440-US.txt and is 15,217 bytes in size.

The present invention relates to immunogenic compositions for use in eliciting immune responses to pathogenic organisms, and in particular, for the prevention of malaria. The invention also provides for the use of the immunogenic compositions, in particular, for use in eliciting a protective immune response.

Plasmodium falciparum malaria is one of the major infectious diseases of mankind. It is the most important parasitic cause of human mortality and a major cause of death in young African children. Current estimates of annual deaths from malaria vary from about 700,000 to over a million. Most of this mortality is in Africa. Additionally there are about 250 million clinical cases of malaria each year, providing a huge burden of morbidity that adds to the disease burden caused by malaria deaths. Although current control measures, such as bed nets, insecticide spraying and rapid drug treatments are partially effective it is widely considered important to develop new tools to control malaria. Probably the most useful of these tools would be an effective malaria vaccine.

Scientists have been attempting to develop a malaria vaccine for over a hundred years (Sergent & Sergent C. R. Acad. Sci. 151:407-409. 1910) and progress has been slow. The most advanced vaccine in clinical development is called RTS,S which has been in clinical development for over 15 years (Gordon et al. J Infect Dis 1995).

The RTS,S vaccine was developed by GSK Biologicals from 1988 to an ongoing phase III trial in African children. This vaccine induces high antibody responses that bind to the major surface component of the malaria sporozoite, the circumsporozoite protein (CS protein), and thereby prevent or reduce parasite entry into the liver (Kester, K. E., et al. J Infect Dis 200, 337-346, 2009). The vaccine is an unusual construct. It comprises a fusion protein of most of the circumsporozoite protein fused at the gene level to the DNA encoding the surface antigen of hepatitis B (HBsAg). This "RTS" (R=repeat, T=T cell epitope containing C-terminus, S=hepatitis B surface antigen) component is co-expressed in the yeast Saccharomyces cerevisiae with a substantial excess of hepatitis B surface antigen (hence RTS, S) with a stochiometry of one part of RTS to four parts of S. This results in only about 14% of RTS,S by mass being part of the P. falciparum CS protein. The excess of S was required to allow RTS to form particles and in turn enhance the immunogenicity of the R component of the vaccine. The generation of such small particles, of about 23 nm in size, often called virus-like particles, is known to be key to enhancing the immunogenicity of many vaccine antigens. However, the disadvantage of this RTS,S particle is that a large part of the immune response, in particular the antibody response, is induced to hepatitis B and only a minority to malaria. Nonetheless, this is the most effective single component vaccine ever tested for malaria and when combined with the saponin+MPL+liposomal formulation adjuvant AS01 reliably induces about 45% sterile efficacy in sporozoite challenge studies (Kester, K. E., et al. J Infect Dis 200, 337-346, 2009), with similar levels of efficacy (39% reduction in episodes over 12 months of follow-up) in a large phase IIb study of 5-17 month old children in Tanzania and Kenya (Olotu, A., et al. Lancet Infect Dis 11, 102-109, 2011).

An aim of the present invention is to provide an alternative immunogen for use in the prevention of malaria, wherein the efficacy of the immunogen is preferably greater than RTS,S.

According to a first aspect the invention provides a particle comprising a fusion protein comprising at least one NANP repeat (SEQ ID NO: 7), some or all of the C-terminus of the CS protein from Plasmodium falciparum and a hepatitis B surface antigen.

Preferably the hepatitis B surface antigen is the S antigen.

The NANP repeat (SEQ ID NO: 7) is a repeat of the four amino acids asparagine, alanine, asparagine, proline which occurs naturally in the CS protein from Plasmodium falciparum. There may be 1, 2, 3, 4, 5, 6, 7, 8, 9, 10, 11, 12, 13, 14, 15, 16, 17, 18 or more repeats of NANP (SEQ ID NO: 8). Preferably there are at least 3 repeats, more preferably there are at least 10 repeats. The fusion protein may in one embodiment comprise 18 repeats of NANP (SEQ ID NO: 9).

The C-terminus of the CS protein is often referred to as the T-cell epitope containing C-terminus. The C-terminus of the CS protein included in the fusion protein of the invention may comprise the sequence:

```
                                         (SEQ ID NO: 6)
NKNNQGNGQGHNMPNDPNRNVDENANANSAVKNNNNEEPSDKHIKEYLN

KIQNSLSTEWSPCSVTCGNGIQVRIKPGSANKPKDELDYANDIEKKICK

MEKCSSVFNVVNSSIGI
``` with some of the C-terminal amino acids deleted. Preferably up to 15 amino acids are deleted, more preferably up to 10 amino acids, 9 amino acids, 8 amino acid, 7 amino acids, 6 amino acids, 5 amino acids, 4 amino acids, 3 amino acids are deleted.

The C-terminus of the CS protein in the fusion protein may have the sequence:

```
                                         (SEQ ID NO: 4)
NKNNQGNGQGHNMPNDPNRNVDENANANSAVKNNNNEEPSDKHIKEYLN

KIQNSLSTEWSPCSVTCGNGIQVRIKPGSANKPKDELDYANDIEKKICK

MEKCSSV.
```

The particle of the invention is sometimes referred to as a virus-like particle. It is considered that such particles are more immunogenic than monomeric proteins.

In the present invention the particle may comprise no, or substantially no, other proteinaceous material.

The particle of the invention may comprise no, or substantially no, free hepatitis B surface antigen protein: that is no, or substantially no, hepatitis B surface antigen protein which is not part of the fusion protein.

The particle of the invention may comprise no, or substantially no, free CS protein: that is no, or substantially no, CS protein which is not part of the fusion protein.

Reference herein to "substantially no" preferably requires the particle to comprise less than about 10%, 9%, 8%, 7%, 6%, 5%, 4%, 3%, 2% or about 1% of the particular material referred. Preferably the particles contain less than 5%, more preferably less than 1%, free hepatitis B surface antigen protein.

Preferably, in a particle of the invention at least about 40% or more by mass of the proteinaceous material is derived from *Plasmodium falciparum*.

The ability to have such a high level of *Plasmodium falciparum* material in the particles allows a more favourable antibody response with respect to malaria, more specifically a significantly improved antibody response to *Plasmodium falciparum* is observed with particles of the invention, and a smaller antibody response is seen to the hepatitis B surface antigen.

A reduction in the relative amount of hepatitis B surface antigen in the particles may also have the advantage that the particles have improved efficacy in early infancy. If too much hepatitis B surface antigen is present there is concern that maternal antibodies present in a young infant may make the particles less effective as immunogens.

Preferably in a fusion protein of the invention the hepatitis B surface antigen is C-terminal to any *Plasmodium falciparum* material.

The particle may comprise a fusion protein comprising, or consisting of, the sequence of Seq ID No: 1 (R21) or a sequence with at least 80%, 85%, 90%, 95%, 98%, 99% or more sequence identity with the sequence of Seq ID No: 1.

Percentage sequence identity is defined as the percentage of amino acids in a sequence that are identical with the amino acids in a provided sequence after aligning the sequences and introducing gaps if necessary to achieve the maximum percent sequence identity. Alignment for the purpose of determining percent sequence identity can be achieved in many ways that are well known to the man skilled in the art, and include, for example, using BLAST (National Center for Biotechnology Information Basic Local Alignment Search Tool).

Variations in percent identity may be due, for example, to amino acid substitutions, insertions or deletions Amino acid substitutions may be conservative in nature, in that the substituted amino acid has similar structural and/or chemical properties, for example the substitution of leucine with isoleucine is a conservative substitution.

Preferably a sequence of Seq ID No: 1 includes sequences with conservative substitutions which do not have any significant effect on the immunogenicity of the resulting fusion protein.

Substitutions may also be introduced to match better the CS sequence of other strains of *Plasmodium falciparum*. The sequence used in the R21 example reported here is of the 3D7 strain.

In an alternative embodiment, the particle may comprise, or consist of, a fusion protein having the sequence of Seq ID No: 2 (RTS) or having a sequence with at least 80%, 85%, 90%, 95%, 98%, 99% or more sequence identity with the sequence of Seq ID No: 2, wherein the particle does not comprise any, or substantially any, hepatitis B surface antigen protein which is not part of the fusion protein.

In another embodiment, the particle may comprise, or consist of, a fusion protein having the sequence of Seq ID No: 2 (RTS) or having a sequence with at least 80%, 85%, 90%, 95%, 98%, 99% or more sequence identity with the sequence of Seq ID No: 2, wherein the particle does not comprise any, or substantially any, CS protein which is not part of the fusion protein.

Preferably a particle of the invention comprises numerous monomers of the fusion protein. The particle may comprise a least 10 fusion protein monomers, preferably 20 or more, 30 or more, 40 or more, 50 or more, 60 or more, 70 or more, 80 or more, 90 or more, 100 or more fusion protein monomers. In one embodiment the particle comprises around 96 fusion protein monomers.

Preferably a particle of the invention is immunogenic. A particle of the invention may be capable of eliciting an immune response against the malaria causing parasite *Plasmodium falciparum*. The immune response may be therapeutic and/or prophylactic. The immune response may be sufficient to reduce or prevent infection or disease cause by *Plasmodium falciparum*. The particle may elicit/produce a protective immune response when administered to a subject, preferably a human subject.

Preferably the immune response elicited by the composition of the invention affects the ability of *Plasmodium falciparum* to infect an immunised human. Preferably the ability of *Plasmodium falciparum* to infect a human immunised with the composition of the invention is impeded or prevented. This may be achieved in a number of ways. The immune response elicited may recognise and destroy *Plasmodium falciparum*. Alternatively, or additionally, the immune response elicited may impede or prevent replication of *Plasmodium falciparum*. Alternatively, or additionally, the immune response elicited may impede or prevent *Plasmodium falciparum* causing disease in the human or non-human animal Preferably the immune response elicited is an antibody response.

The particle may be provided in a liquid formulation. Alternatively, the particle may be provided in a lyophilised form. Alternatively the particle may be provided in a sugar based formulation dried on membranes as described by Alcock et al. (Sci Transl Med. 2010 Feb. 17; 2(19):19ra12).

According to a further aspect the invention provides a method of producing particles according to the first aspect of the invention comprising expressing the fusion protein in *Saccharomyces cerevisiae* or *Pichia pastoris* or another methylotrophic yeast such as *Hansenula polymorpha* and recovering the fusion protein, preferably in the form of particles.

If the fusion protein is expressed in *Pichia pastoris*, or another methylotrophic yeast, expression of the protein may be driven by the AOX1 promoter or by the GAP promoter or by another strong promoter (Vogl & Glieder, New Biotechnology. 2012 Nov. 16. pii: 51871-6784(12)00867-9).

If the fusion protein is expressed in *Saccharomyces cerevisiae*, expression of the protein may be driven by the TDH3 promoter or by another strong promoter.

Preferably the fusion protein is expressed at sufficiently high levels that upon lysis of the yeast the fusion proteins spontaneously multimerise to form particles, sometime referred to as virus-like particles.

The DNA encoding the fusion protein may be transiently or constitutively expressed by the yeast. The DNA encoding the fusion protein may be integrated into the host genome or may be carried on an extracellular component, such as a plasmid. The yeast may contain, 1, 2, 3, 4, 5 or more copies of the DNA encoding the fusion protein.

The DNA encoding the fusion protein may be codon optimised for expression in yeast.

A person skilled in the art would be readily able to prepare a suitable host to express the DNA encoding the fusion protein.

Preferably the *Saccharomyces cerevisiae* or *Pichia pastoris* or another methylotrophic yeast used in the method of the invention does not express any, or any significant, hepatitis B surface antigen protein which is not part of the fusion protein.

Preferably the *Saccharomyces cerevisiae* or *Pichia pastoris* or another methylotrophic yeast used in the method of the invention does not express any, or any significant, CS protein from *Plasmodium falciparum* which is not part of the fusion protein.

The ability to express particles according to the invention in a high yielding yeast strain, such as *Pichia pastoris*, may simplify and enhance the biomanufacture of the particles leading to lower cost of goods for manufacture. This saving in cost is particularly important for a malaria vaccine which is targeted primarily at populations, especially children and infants, in low income countries who require a low cost vaccine.

According to another aspect the invention provides a particle produced by the method of the invention.

According to further aspect the invention provides a host *Saccharomyces cerevisiae* or *Pichia pastoris* or another methylotrophic yeast cell comprising a polynucleotide, such as DNA, encoding for the fusion protein referred to with reference to the particle of the invention.

In one embodiment the invention provides a *Saccharomyces cerevisiae* or *Pichia pastoris* or another methylotrophic yeast cell comprising DNA encoding a fusion protein comprising, or consisting of, the sequence of Seq ID No: 1 (R21) or a sequence with at least 80%, 85%, 90%, 95%, 98%, 99% or more sequence identity with the sequence of Seq ID No: 1. Preferably expression of the DNA is driven by the AOX 1 promoter.

In another aspect the invention provides a DNA sequence encoding a fusion protein referred to with reference to the particle of the invention. The invention may also provide a vector containing the DNA sequence, wherein the DNA sequence may be operably linked to transcriptional control elements.

According to another aspect the invention provides a composition comprising i) a fusion protein comprising at least one NANP repeat (SEQ ID NO: 7), some or all of the C-terminus of the CS protein from *Plasmodium falciparum* and a hepatitis B surface antigen; and ii) a recombinant or non-recombinant viral vector. The viral vector may express an antigen. The viral vector may be a modified vaccinia virus Ankara (MVA). The viral vector may encode TRAP and/or ME-TRAP. Alternatively, or additionally, the antigen expressed by the viral vector may another malaria antigen, such as for example CSP.

The composition may further comprise an adjuvant. The adjuvant may contain saponin and may be Abisco, matrix M, QS21, AS01 or AS02.

The composition may in part i) comprise the fusion protein as a particle as described herein. Alternatively, or additionally, the composition may comprise in part i) the fusion protein RTS, and may further comprise free S antigen from hepatitis B.

According to a still further aspect the invention provides a pharmaceutical composition, and in particular a vaccine composition for use in the prevention of malaria, comprising the particles or composition of the invention and a pharmaceutically acceptable carrier or excipient.

Suitable acceptable excipients and carriers will be well known to those skilled in the art. These may include solid or liquid carriers. Suitable liquid carriers include water and saline. The proteins of the composition may be formulated into an emulsion or they may be formulated into biodegradable microspheres or liposomes.

The composition may further comprise an adjuvant. Suitable adjuvants will be well known to those skilled in the art, and may include Freund's Incomplete Adjuvant (for use in animals), a saponin derivative, an emulsion such as MF59, and metal salts such as aluminium or calcium salts, for example alum. The adjuvant may be a squalene-based adjuvant, such as AddaVax (Invivogen) and/or an ISCOM-based adjuvant, such as Abisco/Matrix M (from Isconova), and/or MF59 (Novartis, Siena, Italy). AddaVax™ is based on nano-emulsification of 2 components: Sorbitan trioleate (0.5% w/v) in squalene oil (5% v/v); and Tween 80 (0.5% w/v) in sodium citrate buffer (10 mM, pH 6.5). The nano-emulsion is produced using a microfluidizer and filtered through a 0.22-μm filter to remove large droplets and sterilize the final product. The particle size is ~160 nm. MF59 is a ~160 nm particle emulsion (Novartis, Siena) comprising Squalene: 9.75 mg; Polysorbate 80: 1.175 mg; Sorbitan trioleate: 1.175 mg; Sodium citrate: 0.66 mg; Citric acid: 0.04 mg. Abisco-100 (known as Matrix-M when made to GMP standard) has the following chemical content: purified saponins obtained from a crude extract of the plant *Quillaja saponaria* Molina; cholesterol from Lanolin and phosphatidyl choline (phospholipid) from fresh egg yolk; in a suspension of nano-sized (40 nm) cage-like particles consisting of the above ingredients, in PBS. Matrix M (or Abisco-100) consists of a mixture of Matrix A and Matrix C at a ratio of 80:20 to 95:5, preferably 85:15. Matrix A leads to T cell induction and has low toxicity, Matrix C induces antibodies and has some toxicity. Matrix C contains C fraction of QS separation which corresponds to QS21. Fraction A (in Matrix A) corresponds to QS7.

The composition may also comprise polymers or other agents to control the consistency of the composition, and/or to control the release of the antigen/secreted protein from the composition.

The composition may also comprise other agents such as diluents, which may include water, saline, glycerol or other suitable alcohols etc; wetting or emulsifying agents; buffering agents; thickening agents for example cellulose or cellulose derivatives; preservatives; detergents; antimicrobial agents; and the like.

Preferably the active ingredients in the composition are greater than 50% pure, usually greater than 80% pure, often greater than 90% pure and more preferably greater than 95%, 98% or 99% pure. With active ingredients approaching 100% pure, for example about 99.5% pure or about 99.9% pure, being used most often.

The composition of the invention may also include in admixture one or more further antigens. The one or more further antigens may be derived from *Plasmodium falciparum* or from other species of *Plasmodium*, such as *Plasmodium vivax* or *Plasmodium malariae*.

The pharmaceutical composition or vaccine composition may be provided in a liquid form or in a lyophilised form.

The pharmaceutical composition or vaccine composition may be intended for administration in a dose selected to give an appropriate immune response whilst not causing significant side affects. Each dose may comprise between about 1 and about 1000 μg of fusion protein, for example between about 1 and about 200 μg of fusion protein, preferably between about 1 and about 50 μg of fusion protein. The optimal amount of particles/fusion protein to be used can be ascertained by standard studies well known to a person skilled in the art.

Preferably the pharmaceutical composition or vaccine composition is capable of producing a protective immune response to *Plasmodium falciparum*.

The phrase "producing a protective immune response" as used herein means that the composition is capable of generating a protective response in a host organism, such as a human or a non-human mammal, to whom it is administered. Preferably a protective immune response protects against subsequent infection or disease caused by *Plasmodium falciparum*. The protective immune response may eliminate or reduce the level of infection by reducing replication of *Plasmodium falciparum* or by affecting the mode of action of *Plasmodium falciparum* to reduce disease.

Preferably, if the composition is used as a vaccine, the composition comprises an immunologically effective amount of particles according to the invention. An "immunologically effective amount" of an antigen is an amount that when administered to an individual, either in a single dose or in a series of doses, such as 2 to 4 doses, is effective for treatment or prevention of infection by *Plasmodium falciparum*. This amount will vary depending upon the health and physical condition of the individual to be treated and on the antigen. Determination of an effective amount of an immunogenic or vaccine composition for administration to an organism is well within the capabilities of those skilled in the art.

A composition according to the invention may be for oral, systemic, parenteral, topical, mucosal, intramuscular, intravenous, intraperitoneal, intradermal, subcutaneous, intranasal, intravaginal, intrarectal, transdermal, sublingual, inhalation or aerosol administration.

The composition may be arranged to be administered as a single dose or as part of a multiple dose schedule. Multiple doses may be administered as a primary immunisation followed by one or more booster immunisations. Suitable timings between priming and boosting immunisations can be routinely determined, but will typically be at intervals of 2 weeks to 4 months.

Compositions of the invention may be able to induce serum antibody responses which mediate the destruction or inactivation of the *Plasmodium falciparum* after being administered to a subject. These responses are conveniently measured in mice and the results are a standard indicator of vaccine efficacy.

The compositions of the invention may also, or alternatively, be able to elicit an immune response which neutralises *Plasmodium falciparum*, thereby preventing them from having their normal function and preventing or reducing disease progression without necessarily destroying the *Plasmodium falciparum*.

A composition according to the invention may be used in isolation, or it may be combined with one or more other immunogenic or vaccine compositions, and/or with one or more other therapeutic regimes.

The composition may be intended for administration with a viral vector. The viral vector may encode one or more pre-erythrocytic malaria antigens or antigens from other stages of the malaria parasite's life-cycle. The antigen encoded may be the malarial antigen TRAP (thrombospondin related adhesion protein) or ME-TRAP. The strong T cell immunogenicity of such vectored vaccines that are known to have some partial efficacy against the liver-stage of malaria infection, is either maintained or even, surprisingly, enhanced when combined with a composition of the invention. The invention may provide a combination malaria vaccine, comprising particles according to the invention and a viral vector. The combination would have potent anti-sporozoite activity primarily induced by the particles and anti-liver-stage activity primarily induced by the viral vectors.

The composition may be intended to be administered with one or more of an adenovirus vector and an MVA vector. The composition may be administered in a prime boost regimen, wherein the prime comprises the particles of the invention and an adenovirus vector or an MVA vector, and the boost comprises the particles of the invention and adenovirus or an MVA vector. Preferably the prime comprises an adenovirus and boost comprises an MVA vector. Preferably the prime and the boost include an adjuvant with the particles. The adenoviral vector or the MVA viral vectors and the particles of the invention may be administered as a mixture, or alternatively they may be administered separately, meaning at separate immunisation sites or at separate time points. If administered separately the vector and particles may be administered at the same or different sites. The administration of vector and particles may be simultaneous, or substantially simultaneous, for example, within 10 minutes of each other, or the administration may be sequential. Preferably if the vector and particles are administered sequentially, they are administered within at most about 30 days, 7 days, 6 days, 4 days, 2 days, 24 hours or less, of each other.

The composition of the invention may further comprise one or more viral vectors.

According to yet another aspect the invention provides a fusion protein comprising the sequence of Seq ID No: 1 (R21) or comprising, or consisting of, a sequence with at least 80%, 85%, 90%, 95%, 98%, 99% or more sequence identity with the sequence of Seq ID No: 1. Preferably the fusion protein consists of the sequence of Seq ID No: 1 (R21).

According to a further aspect the invention provides a method of treating a subject susceptible to *Plasmodium falciparum* infection comprising administering to the subject an effective amount of a pharmaceutical composition or vaccine composition according to the invention.

According to a further aspect the invention provides a method of immunising a subject against malarial *Plasmodium falciparum* infection comprising administering to the subject an effective amount of a pharmaceutical composition or vaccine composition according to the invention.

According to another aspect the invention provides a use of a pharmaceutical composition or vaccine composition according to the invention in the preparation of a medicament for the treatment/immunisation of a subject susceptible to *Plasmodium falciparum* infection.

According to another aspect the invention provides a pharmaceutical composition or vaccine composition according to the invention for use in the treatment/immunisation of a subject susceptible to *Plasmodium falciparum* infection.

According to further aspect the invention provides a kit for use in inducing an immune response to *Plasmodium falciparum* comprising a particle or composition according to the invention and instructions relating to administration. The kit may further comprise one or more of an adjuvant and a viral vector. If an adjuvant is present preferably it is in the same composition as the particle. The viral vector may be in a same of different composition to the particle.

The skilled man will appreciate that any of the preferable features discussed above can be applied to any of the aspects of the invention.

Preferred embodiments of the present invention will now be described, merely by way of example, with reference to the following figures and examples.

Figure 3:
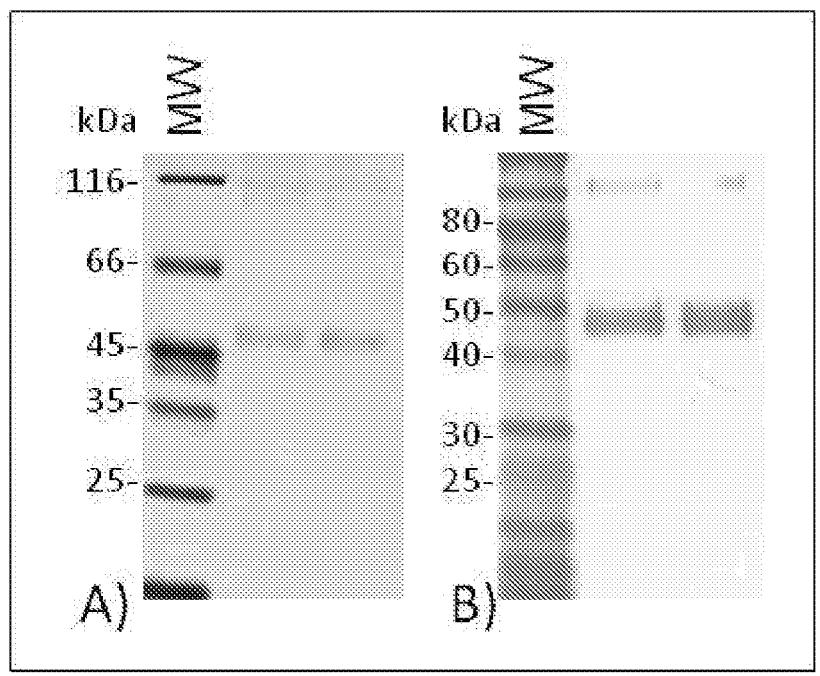

FIG. 1—provides the sequence of R21 (Seq ID No: 1) and RTS (Seq ID No: 2);

FIG. 2—shows the results of the analysis of purified R21 particles by transmission electron microscopy—FIG. 2A. In FIG. 2B particles are shown that lack the 105 amino acid of the CS protein C terminus. The particles are negatively stained with 2% uranyl acetate;

FIG. 3—shows the results of the analysis of R21 purified particles by reducing gel electrophoresis. FIG. 3A shows silver stained R21 purified particles. FIG. 3B shows the results of a western blot using monoclonal anti-NANP antibody ("NANP" disclosed as SEQ ID NO: 7; from MR4, named 2A10).

Figure 4:
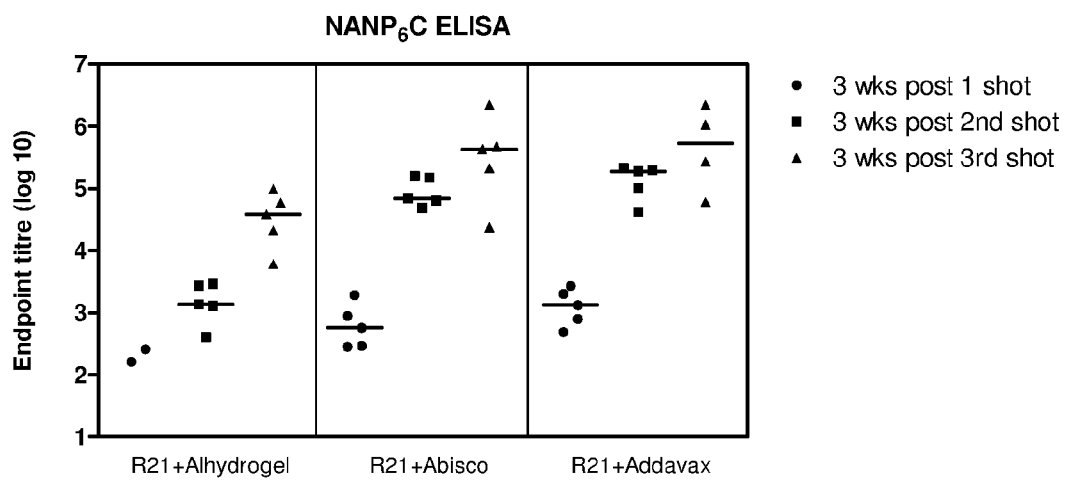

FIG. 4—shows the results of immunisation studies. BALB/c mice were immunised intramuscularly with 0.5 μg R21 with either Alhydrogel (85 ug) or Abisco-100 (12 ug) or AddaVax. Three shots were given 3 weeks apart and NANP-specific antibody ("NANP" disclosed as SEQ ID NO: 7) responses were assayed by ELISA 3 weeks after each immunisation. Median responses are shown. "NANP$_6$C" disclosed as SEQ ID NO: 12.

Figure 5:
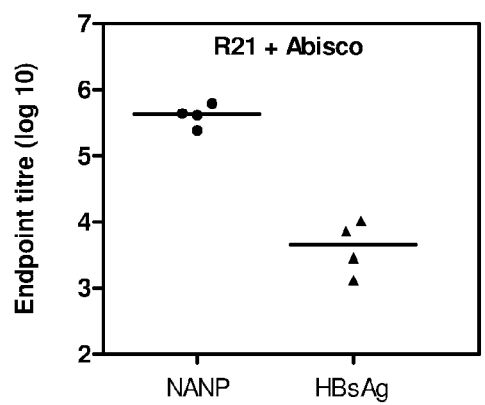

FIG. 5—demonstrates that R21 in Abisco adjuvant induced high titre antibodies to the NANP repeat (SEQ ID NO: 7) of the CS protein but modest antibody titres to HBsAg. BALB/c mice were immunised intramuscularly with 5 μg R21 with Abisco-100. Three shots were given 3 weeks apart and HBsAg-specific antibody responses were assayed by ELISA 3 weeks after the 3rd immunisation. Median responses are shown.

Figure 6:
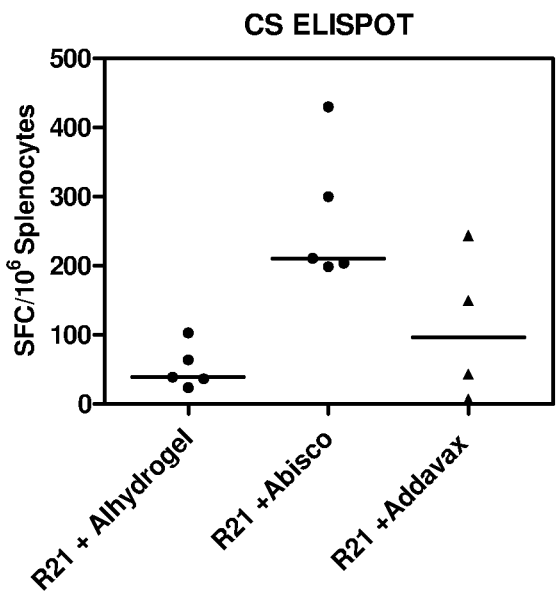

FIG. 6—details the results of IFN-γ Spleen ELISpot analysis for BALB/c mice immunised intramuscularly with 0.5 μg R21 with either Alhydrogel (85 ug) or Abisco-100 (12 ug) or AddaVax. Three shots were given 3 weeks apart and NANP-specific antibody ("NANP" disclosed as SEQ ID NO: 7) responses were assayed by ELISA 3 weeks after each immunisation. Median responses are shown.

Figure 7:
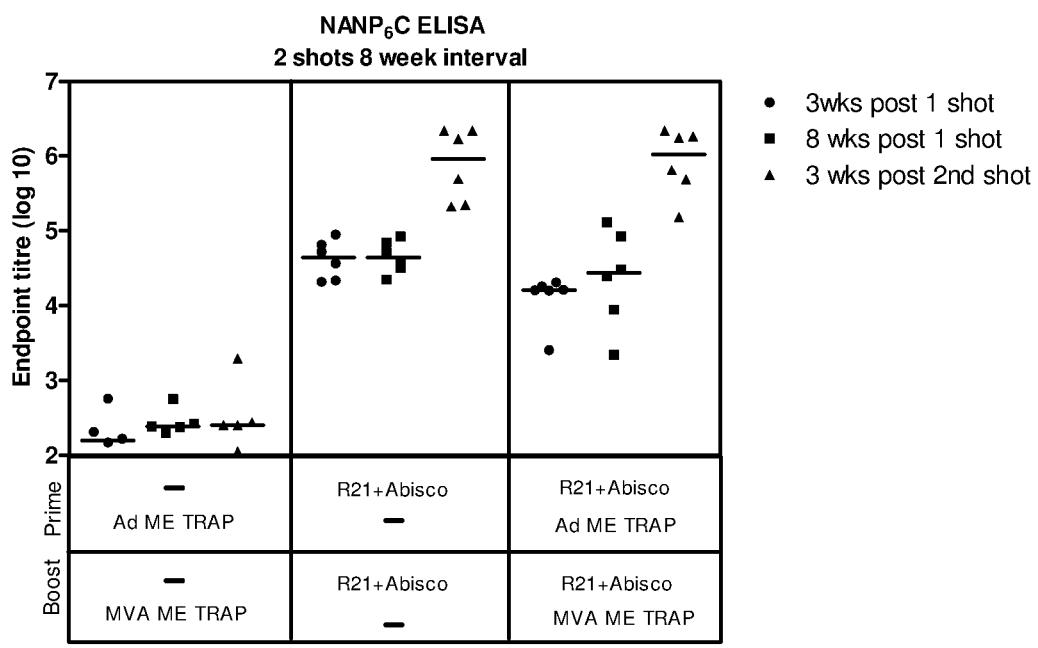

FIG. 7—demonstrates that R21 in adjuvant can be combined with viral vectors without impairing humoral immunogenicity. BALB/c mice were immunised with either 2 shots of R21+Abisco-100 or the ChAd63 (Ad) ME TRAP-MVA ME TRAP 8 week prime-boost regime alone or combined together, as detailed in Table 1. Humoral responses were assayed in the NANP (SEQ ID NO: 7) ELISA carried out 3 weeks and 8 weeks after the first immunisation, and 3 weeks after the final immunisation. Median responses are shown. No impairment of the humoral immunogenicity of R21 is observed. "NANP$_6$C" disclosed as SEQ ID NO: 12.

FIG. 8—demonstrates that R21 in adjuvant can be combined with viral vectors without impairing T cell immunogenicity. BALB/c mice were immunised with either 2 shots of R21+Abisco-100 or the ChAd63 (Ad) ME TRAP-MVA ME TRAP 8 week prime-boost regime alone or combined together. Cellular responses were assayed in an IFN-γ spleen ELISpot to a pool of CS peptides (A) or the Pb9 peptide (B) 3 weeks after the final immunisation. Median responses are shown. No impairment of the T cell immunogenicity of R21 or the viral vectors is observed.

Figure 9:
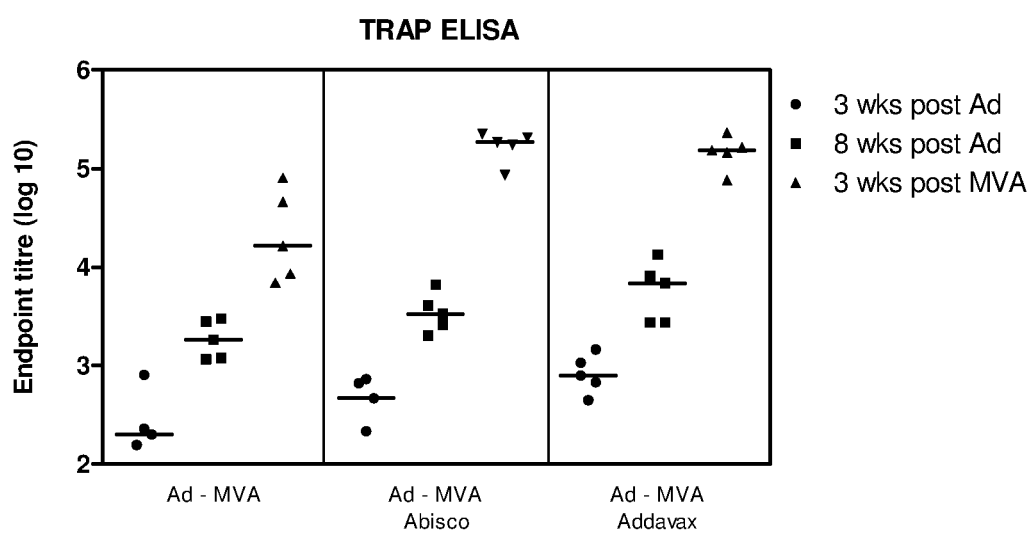

FIG. 9—demonstrates that mixing R21 plus adjuvants with vectors can enhance antibody responses to the vector encoded antigen. BALB/c mice were immunised intramuscularly with the ChAd63 (Ad) ME TRAP-MVA ME TRAP 8 week prime-boost regime alone or combined with either Abisco-100 or AddaVax. TRAP-specific antibody responses were assayed by ELISA 3 weeks and 8 weeks after the first immunisation and 3 weeks after the second Median responses are shown.

Figures 10, 11:
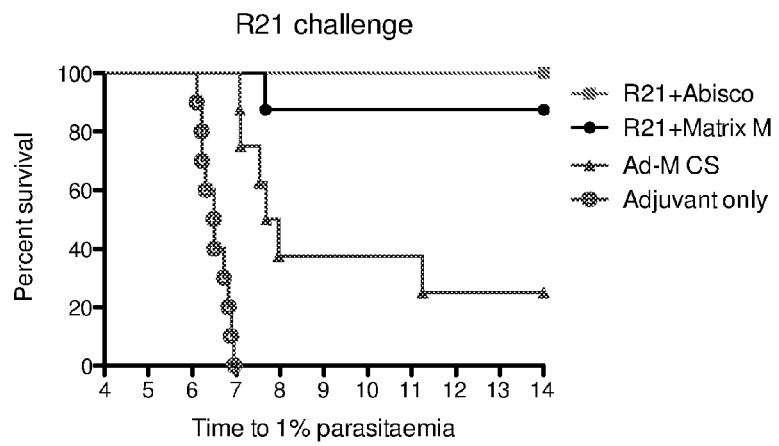

FIG. 10—demonstrates that the R21 in a ISCOM adjuvant, such as Abisco or Matrix M (available from Isconova, Uppsala, Sweden) provides high level protective efficacy against malaria sporozoite infection in mice. The mice were infected at two immunisations with the R21 particle in adjuvant by a transgenic Plasmodium berghei parasite, transgenic for the P. falciparum CS protein gene. Such parasites are described in the research literature (Tewari R et al. J Biol Chem. 2002 Dec. 6; 277(49):47613-8; Kaba S et al. PLoS One. 2012; 7(10):e48304). The results demonstrate that the R21 particle not only shows excellent immunogenicity against P. falciparum CS but potent efficacy in a very relevant malaria infection model. IM: intramuscular.

FIG. 11—this table illustrates the study design used to consider the immunogenicity of R21 without an adjuvant.

Figure 12:
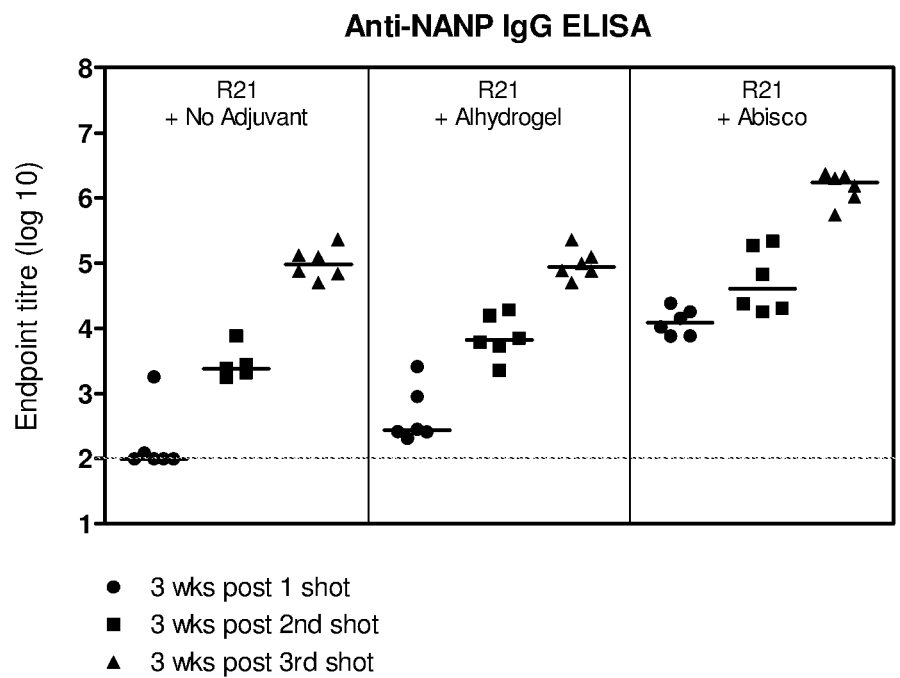

FIG. 12—demonstrates CS-specific IgG responses to R21 with different adjuvants. BALB/c mice were immunised intramuscularly with 0.5 ug R21 alone or formulated with Alhydrogel or Abisco-100. Three immunisations were given three weeks apart and the NANP-specific antibody ("NANP" disclosed as SEQ ID NO: 7) titres were measured by ELISA 3 weeks after each immunisation. Median responses are shown.

Figure 13:
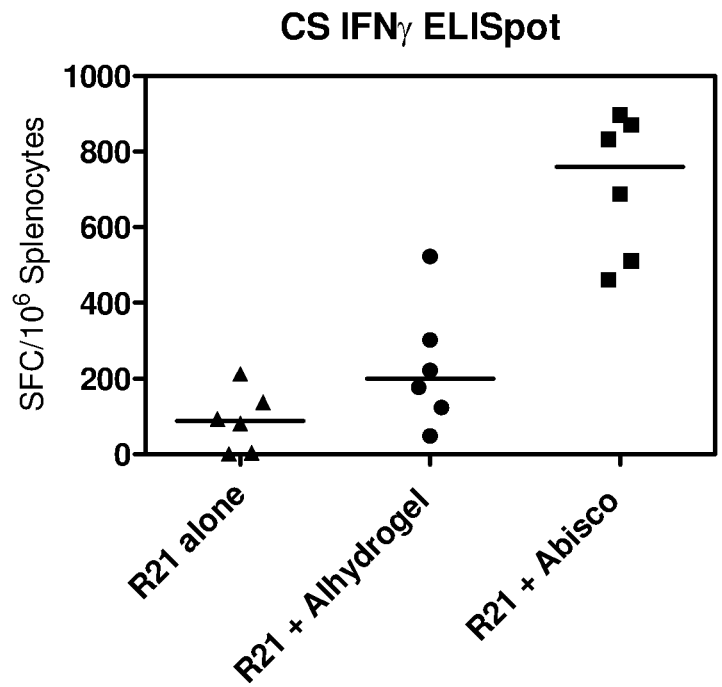

FIG. 13—demonstrates IFN-γ Spleen ELISpot responses to R21 with Matrix M. BALB/c mice were immunised intramuscularly with 0.5 μg R21 with Matrix M (12 ug). Three shots were given 3 weeks apart and CS-specific T cell responses were measured in the spleen by IFN-γ ELISpot 3 weeks after the final immunisation. Median responses are shown.

Figures 14, 15:
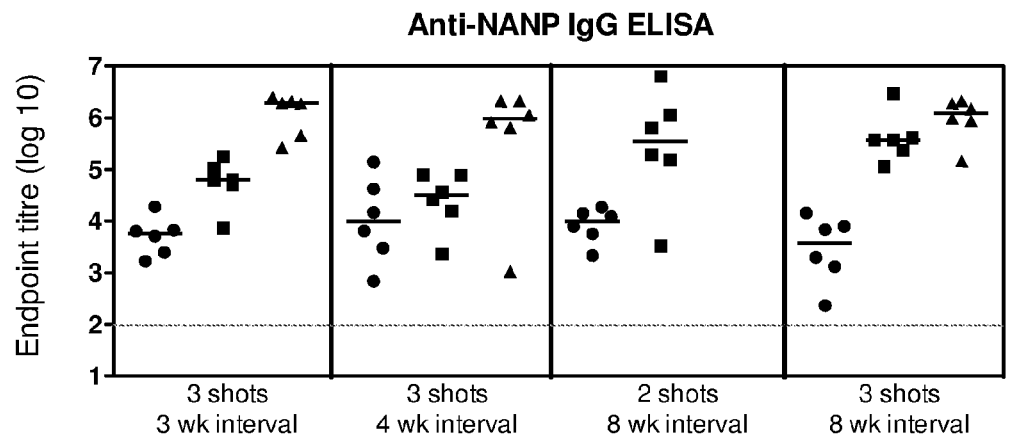

FIG. 14—illustrates the study design for a vaccine immunisation interval study. The illustrated vaccine regimens were used to assess the immunogenicity of R21+Matrix M in BALB/c mice FIG. 15—demonstrates CS-Specific IgG responses to R21 and Matrix M. BALB/c mice were immunised intramuscularly with 0.5 μg R21 with Matrix M (12 ug). NANP-specific antibody ("NANP" disclosed as SEQ ID NO: 7) titres were assayed by ELISA 3 weeks after each immunisation. Median responses are shown.

Figures 16, 17:
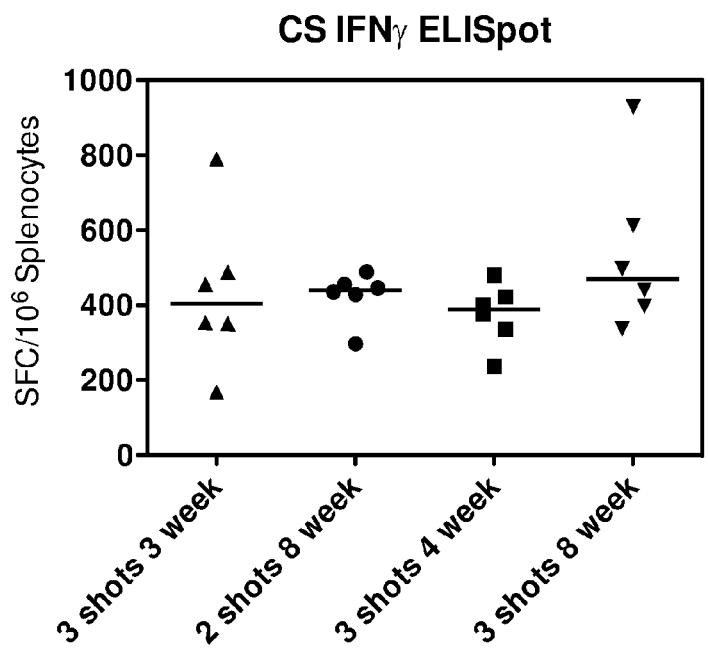

FIG. 16—demonstrates IFN-γ Spleen ELISpot responses to R21 and Matrix M. BALB/c mice were immunised intramuscularly with 0.5 μg R21 with Matrix M (12 ug). Three shots were given 3 weeks apart and CS-specific T cell responses were measured in the spleen by IFNg ELISpot 3 weeks after the final immunisation. Median responses are shown.

Figure 18:
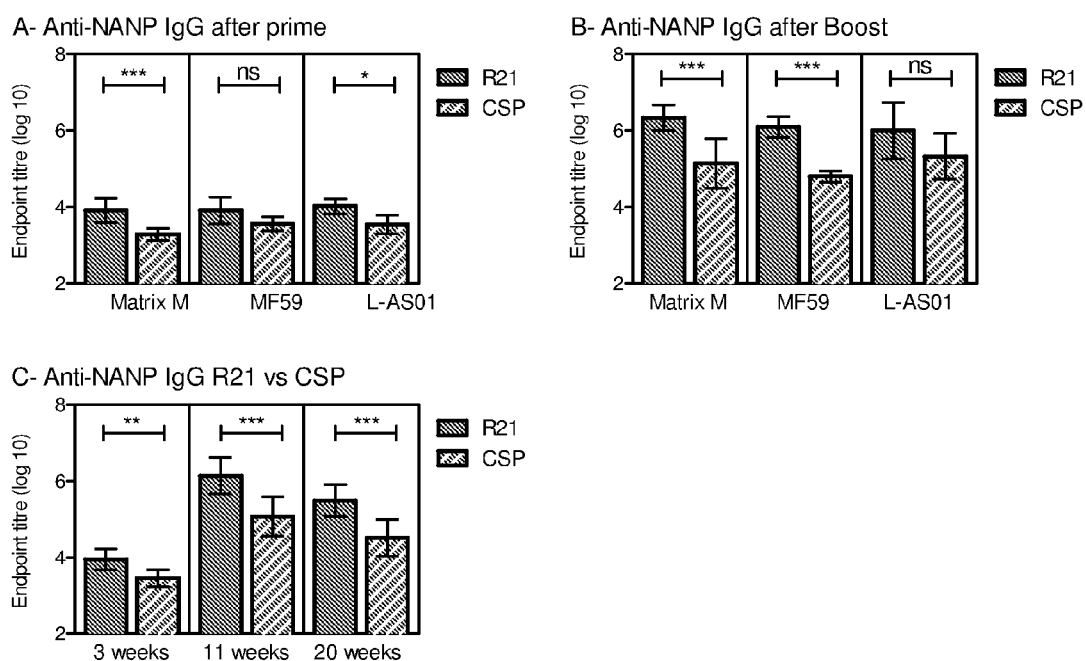

FIG. 17—shows the study design used to compare R21 and the CSP recombinant protein FIG. 18—demonstrates CS-specific IgG responses to R21 or CSP with either Matrix M, MF59 or L-AS01. BALB/c mice were immunised intramuscularly with 0.5 μg R21 or CSP with either Matrix M, MF59 or L-AS01. NANP-specific antibody ("NANP" disclosed as SEQ ID NO: 7) titres were assayed by ELISA 3 weeks after each immunisation. Mean responses with SD are shown (Groups compared by One-way ANOVA with Bonferroni's post-test. ns=non-significant, * p<0.05, p<0.01, *p<0.001).

Figure 19:
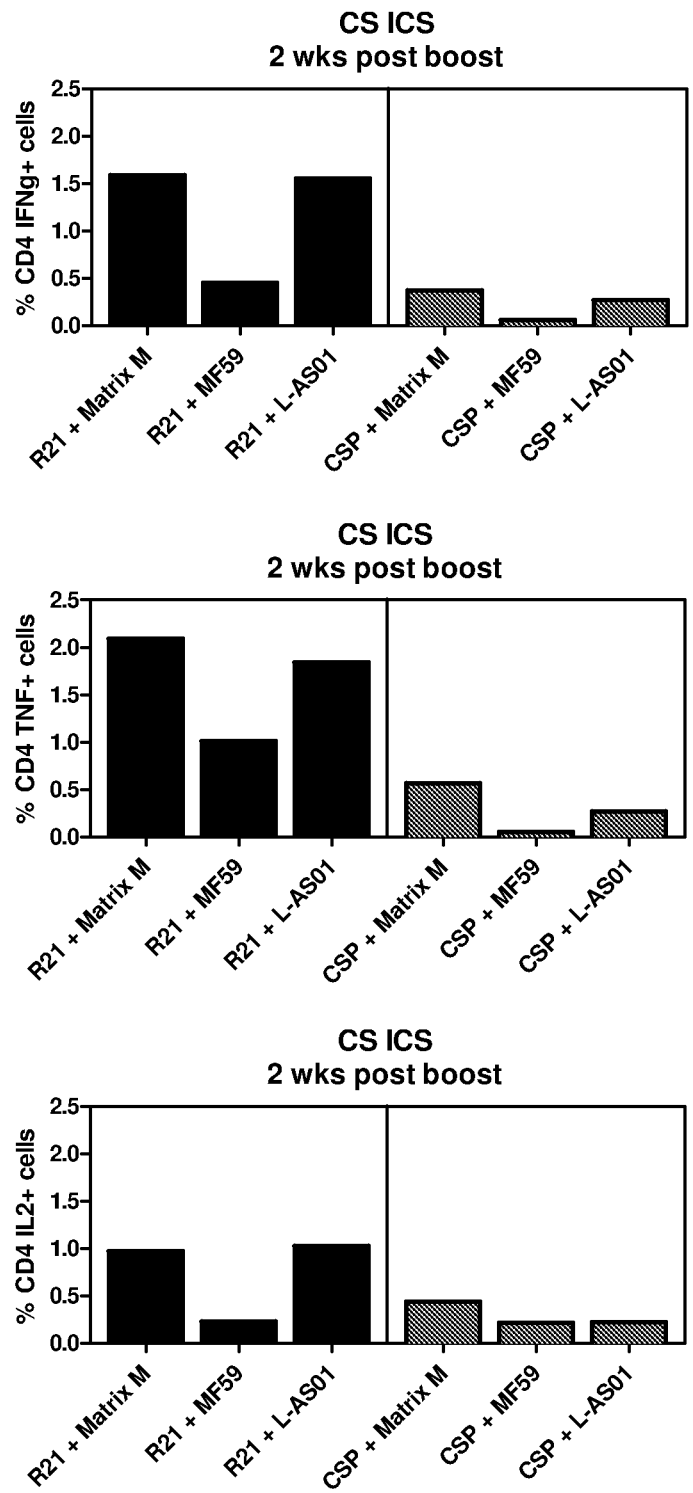

FIG. 19—demonstrates CS-specific T cells to R21 or CSP with either Matrix M, MF59 or L-AS01. CS-specific T cells. BALB/c mice were immunised intramuscularly with 0.5 μg R21 or CSP with either Matrix M, MF59 or L-AS01. CS specific T cell responses were measured in the blood by ICS and flow cytometry, 2 weeks after the boost vaccination.

Isolated PBMC's were re-stimulated with a pool of CS peptides and frequencies of cytokine secreting CD4+T cells were measured (IFNg, TNF and IL2). Mean responses shown.

Figure 20:
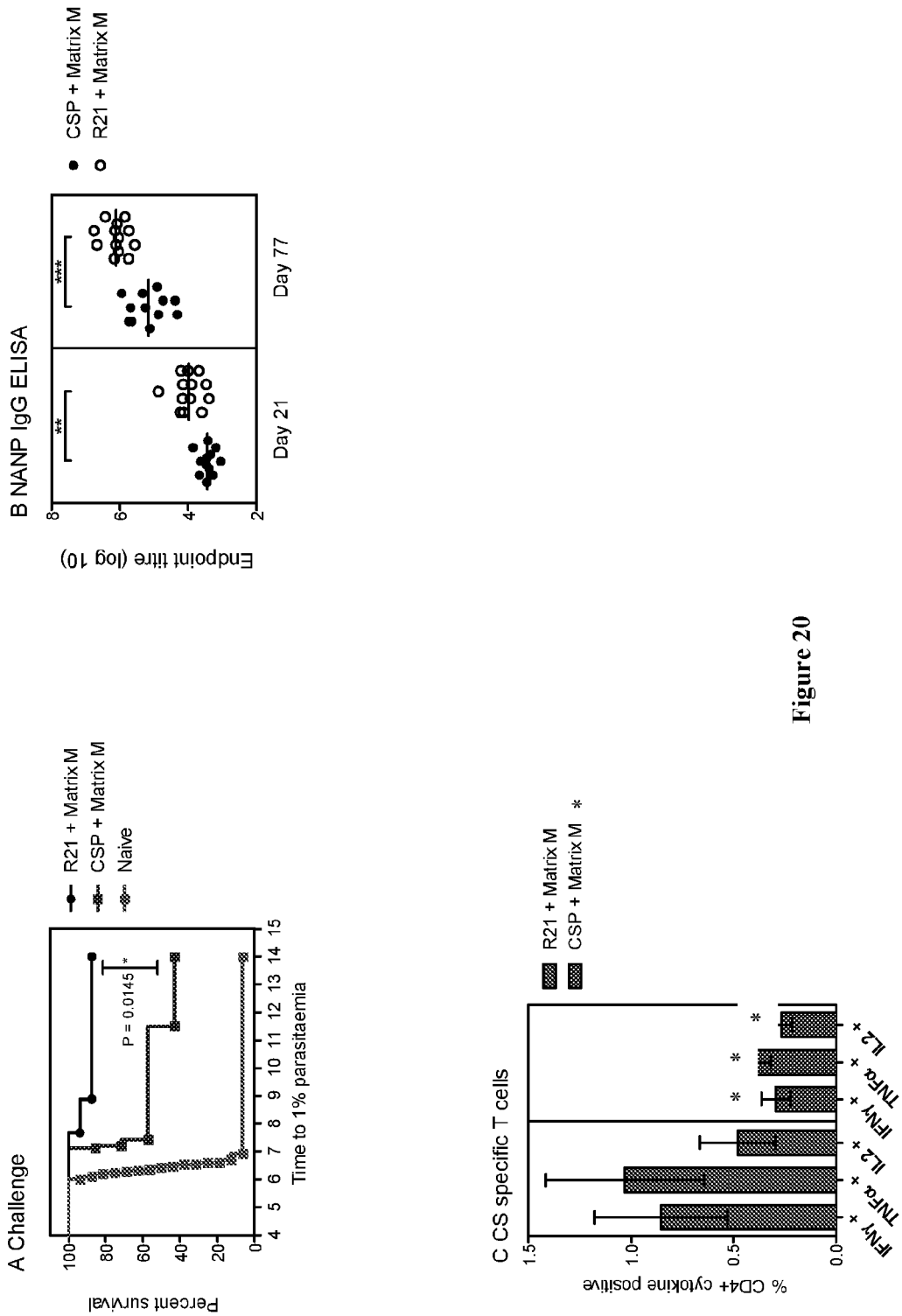

FIG. 20—illustrates an R21 vs CSP challenge experiment. BALB/c mice were immunised intramuscularly with two shots of 0.5 μg R21 or CSP with Matrix M, 8 weeks apart. A) Mice were challenged 3 weeks after boost with 1000 sporozoites injected i.v. and time to 1% parasitemia was determined by thin film blood smear from day 5 post challenge. Mice were sterilely protected if they had no blood stage parasites by day 14. Survival curves compared by Log-rank (Mantel-Cox) Test. B) NANP-specific antibody ("NANP" disclosed as SEQ ID NO: 7) titres were assayed by ELISA 3 weeks after each immunisation. Mean responses with SD are shown (Groups compared by One-way ANOVA with Bonferroni's post-test. p<0.01, *p<0.001). C) T cell responses were measured in the blood by ICS and flow cytometry, 2 weeks after the boost vaccination. Isolated PBMC's were re-stimulated with a pool of CS peptides and frequencies of cytokine secreting CD4+T cells were measured secreting (IFNg, TNF and IL2). Mean responses with SEM are shown.

Figure 21:
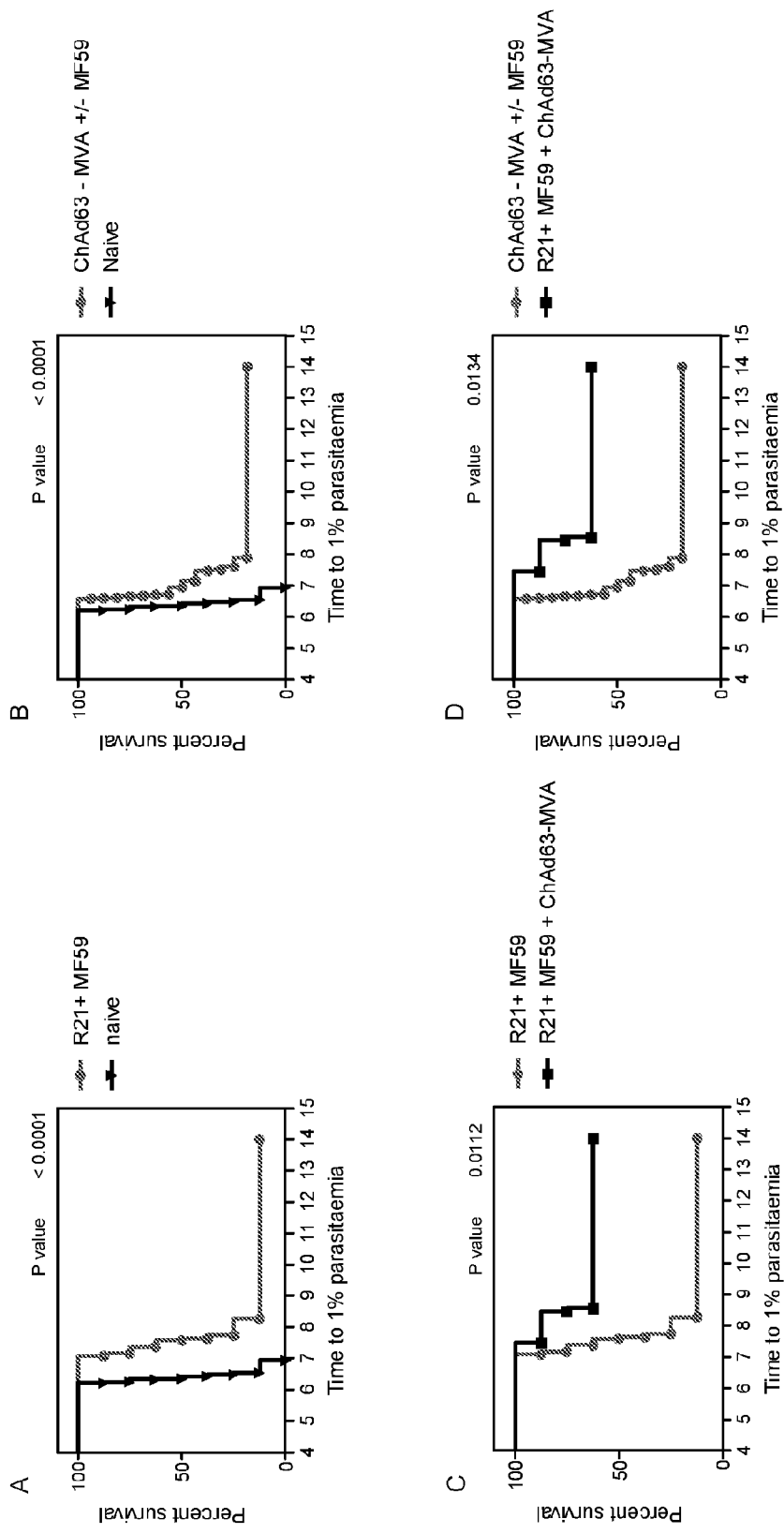

FIG. 21—demonstrates the enhanced efficacy of combined immunisation with R21 and viral vectors. BALB/c mice were immunised intramuscularly with R21+MF59 or the ChAd63 PbTRAP-MVA PbTRAP regimen alone (A or B) or combined together (C and D). Mice were challenged 3 weeks after boost with 1000 sporozoites injected i.v. and time to 1% parasitemia was determined by thin film blood smear from day 5 post challenge. Mice were sterilely protected if they had no blood stage parasites by day 14. Survival curves were compared by Log-rank (Mantel-Cox) Test.

Figure 22:
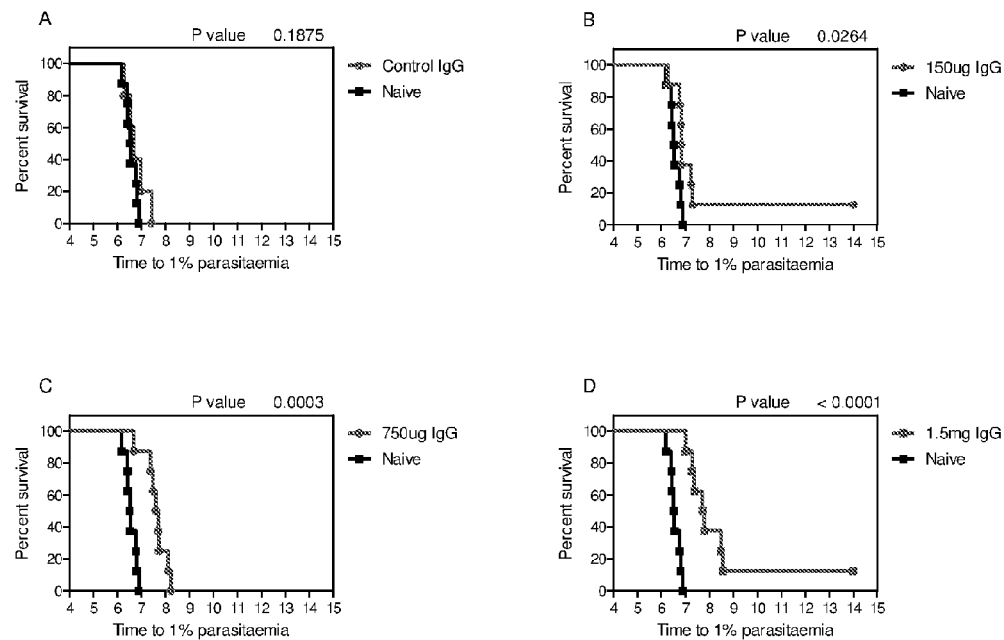

FIG. 22—demonstrates the efficacy of IgG passive transfer. BALB/c mice were immunised intramuscularly with R21+Matrix M twice, 8 weeks apart, mice were bled and total IgG was purified. Naïve mice were immunised with either B) 150 ug C) 750 ug or D) 1.5 mg of total IgG from vaccinated mice i.v. A control group also received IgG from unvaccinated mice A). All mice were challenged 5 hours after IgG transfer with 1000 sporozoites injected i.v. and time to 1% parasitemia was determined by thin film blood smear from day 5 post challenge. Mice were sterilely protected if they had no blood stage parasites by day 14. Survival curves were compared by Log-rank (Mantel-Cox) Test.

Figure 23:
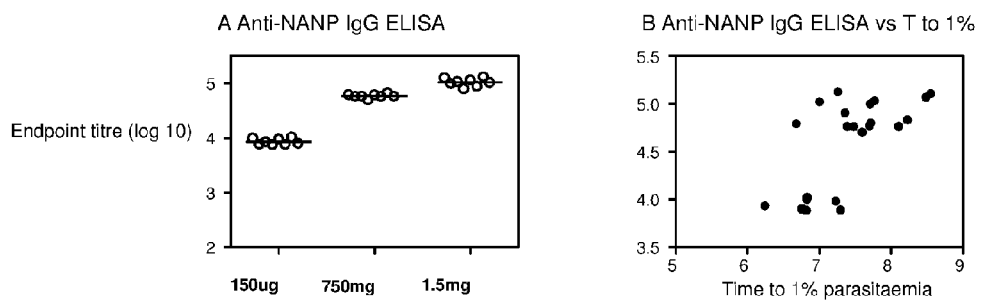

FIG. 23—demonstrates that NANP-specific IgG ("NANP" disclosed as SEQ ID NO: 7) correlates with efficacy. Groups of BALB/c mice received increasing doses of total IgG from vaccinated mice (R21+Matrix M) and had moderate—good levels of NANP-specific IgG ("NANP" disclosed as SEQ ID NO: 7) titres at the time of challenge (A). The level of NANP-specific IgG ("NANP" disclosed as SEQ ID NO: 7) correlated with the time taken for mice to develop 1% parasitemia (B) (correlation tested using Pearsons correlation, p=0.0008, r=0.659).

In order to exemplify the invention described herein particles comprising the fusion protein R21 (Seq ID no: 1, FIG. 1) were produced and their immunogenic properties were considered.

Development of R21 Expressing Yeast
Materials and Methods
R21 Expression Plasmid A sequence which encodes for the fusion protein R21 (Seq ID No: 1 and FIG. 1) of was cloned into the pPink-HC expression plasmid from the PichiaPink™ Expression System (Invitrogen, Cat. no. A11150).

The R21 protein comprises the Hepatitis B surface antigen (HBsAg) adw serotype and a C-terminal portion of the circumsporozoite (CS) protein of the *Plasmodium falciparum* strain NF54. The sequence comprises 410 amino acids from N to C terminus:

75 amino acids of the NANP repeat ("NANP" disclosed as SEQ ID NO: 7) from the CS protein—comprising MDP followed by 18 NANP repeats ("18 NANP repeats" disclosed as SEQ ID NO: 9):

(SEQ ID NO: 3)
MDPNANPNANPNANPNANPNANPNANPNANPNANPNANPNANPNANPNA

NPNANPNANPNANPNANPNANPNANP 105 amino acid of the CS protein C terminus:

(SEQ ID NO: 4)
NKNNQGNGQGHNMPNDPNRNVDENANANSAVKNNNNEEPSDKHIKEYLN

KIQNSLSTEWSPCSVTCGNGIQVRIKPGSANKPKDELDYANDIEKKICK

MEKCSSV (The 10 C terminal amino acids (FNVVNSSIGL (SEQ ID NO: 10)) of the CS protein have been removed.)

4 amino acids from the pre-S2 region of the hepatitis B virus:

(SEQ ID NO: 11)
PVTN followed by 226 amino acids of the HBsAg adw serotype:

(SEQ ID NO: 5)
MENITSGFLGPLLVLQAGFFLLTRILTIPQSLDSWWTSLNFLGGSPVCL

GQNSQSPTSNHSPTSCPPICPGYRWMCLRRFIIFLFILLLCLIFLLVLL

DYQGMLPVCPLIPGSTTTNTGPCKTCTTPAQGNSMFPSCCCTKPTDGNC

TCIPIPSSWAFAKYLWEWASVRFSWLSLLVPFVQWFVGLSPTVWLSAIW

MMWYWGPSLYSIVSPFIPLLPIFFCLWVYI

R21 Expressing Yeast

PichiaPink™ Strain 4 (Invitrogen, Cat. no. A11150), which is a double knock-out for proteinases A and B (i.e. pep4 and prb1), was transformed by electroporation with the pPink-HC expression plasmid encoding R21. Positively transformed colonies were selected by growth on adenine deficient agar plates.

Initial Characterisation of Transformed Yeast

Positive colonies were selected and grown in small 1 mL pilot expression cultures and protein expression induced by the addition of methanol. Levels of protein expression in each clone were then analysed by western blot. Induced R21 expressing yeast samples were disrupted in laemmli lysis buffer and western blot analysis was performed using an antibody to the NANP repeat (SEQ ID NO: 7) in the CSP portion of the fusion protein, (monoclonal anti-NANP antibody ("NANP" disclosed as SEQ ID NO: 7) (MR4, 2A10)) and a monoclonal anti-HBsAg antibody (Serotec, MCA4658). Expression of the fusion protein that was recognised by both antibodies at the correct size was confirmed.

Growth of *Pichia Pastoris* and Induction of R21 Expression

One R21 expressing clone was selected and grown in a 1 L batch culture with BMGY (Buffered complex medium containing glycerol). R21 expression was induced by the addition of methanol by changing the media to BMMY (Buffered complex medium containing methanol). Expression was induced with 0.5% methanol for 3 days at which point the yeast was pelleted by centrifugation at 1,500×g for 5 minutes, the supernatant removed and the yeast frozen at −80° C.

Extraction and Purification of R21

Cell Disruption

Yeast pellets were thawed on ice and resuspended in a lysis buffer containing 10 mM Tris (pH 7.8), 0.1% Triton X-100, 1 mM EDTA. Acid washed glass beads (0.425-600 um) were added and the sample was disrupted by 10 cycles of vortexing for one minute then placing on ice for one minute.

Purification

Clarification

Before purification the yeast debris was removed by centrifugation for 5 minutes at 1,500×g and this lysate was then clarified by ultracentrifugation at 13,000×g for 20 minutes.

CsCl Discontinuous Gradient Centrifugation

The clarified lysate was then layered onto a discontinuous CsCl gradient containing layers of 1.3 g/ml CsCl and 1.1 g/ml CsCl. After ultracentrifugation for 2 hours at 41,000 rpm in a SW41 Ti rotor, (Beckman Coulter Optima L-100 XP) the particle containing fraction was collected.

Gel Filtration

The particle containing fraction was then applied to a PD10 column containing Sephedex G100. The sample was eluted in 10 mM Tris (pH7.8) and particle containing fractions were collected and pooled.

CsCl Isopycnic Gradient Centrifugation

The pooled sample was then added to an isopycnic CsCl gradient containing 1.2 g/ml CsCl. After ultracentrifugation for 20 hours at 41,000 rpm in a SW41 Ti rotor, (Beckman Coulter Optima L-100 XP) the particle containing fraction was collected.

Size Exclusion Chromatography on Sephacryl 500

The sample was then applied to a Hiprep 16/60 Sephacryl S-500 HR gel filtration column (GE Healthcare) to exchange the buffer and remove any remaining lower molecular weight contaminants. The sample was eluted in 10 mM Tris buffer (pH7.8) and pure particle containing fractions were pooled.

R21 Characterisation

Electron Microscopy

To confirm the presence and size of particles, the purified R21 particle preparation was analysed by negative staining with 2% uranyl acetate on a transmission electron microscope (FIG. 2A). Particles appear to be approximately 22 nm in size.

Particles were also made that lacked the 105 amino acid of the CS protein C terminus, these are depicted in FIG. 2B.

Gel Electrophoresis; Silver Stain and Western Blot Analysis

The purified R21 particle preparation was analysed by reducing gel electrophoresis. The sample was silver stained to assess the purity and analysed by western blotting with a monoclonal anti-NANP antibody ("NANP" disclosed as SEQ ID NO: 7; MR4, 2A10) and an anti-HBsAg monoclonal antibody to assess the immunoreactivity of the product. The same band was recognised by both antibodies and the purified product was greater than 90% pure based on the silver stained gel (FIG. 3).

ELISA to CS Repeat Region

The presence and accessibility of the NANP repeat (SEQ ID NO: 7) region on the surface of the particle was assessed by sandwich ELISA using two antibodies to the NANP repeat ("NANP" disclosed as SEQ ID NO: 7) region. Maxisorb 96 well plates (Nunc) were coated with mouse monoclonal anti-NANP antibody ("NANP" disclosed as SEQ ID NO: 7; MR4, 2A10), incubated with purified R21 particle and a rabbit polyclonal serum (MR4, MRA-24) was used for detection. The purified R21 particle prep gave a strong positive signal.

ELISA to CS Repeat Region and HBsAg

The presence and accessibility of the HBsAg portion of fusion protein in the particle was assessed by sandwich ELISA using a monoclonal antibody to the NANP repeat (SEQ ID NO: 7) region (MR4, 2A10) and a cocktail of antibodies to the HBsAg from Monolisa ULTRA HBsAg ELISA kit (Biorad). The purified R21 particle prep gave a weak positive signal thus confirming the presence and accessibility of the HBsAg epitopes on the same NANP (SEQ ID NO: 7) containing R21 particles.

Quantification by Absorbance at 280 nm

The purified particle prep is quantified by measuring absorbance at 280 nm.

Larger Scale Manufacturing of R21

To assess the feasibility of larger scale manufacturing a new process was developed in a GMP facility approved by the UK Medicines and Healthcare products Regulatory Agency (MHRA), the Clinical Biomanufacturing Facility at the University of Oxford. This large scale process provided satisfactory yields of R21 particles at a larger scale that were immunogenic in small animals, indicating that a GMP compatible process is achievable for clinical grade manufacturing of the R21 particle immunogen.

Immunogenicity of R21 Particles in Mice

Immunogenicity was assessed in mice by measuring the antibodies generated to the NANP repeat (SEQ ID NO: 7) in an ELISA and by measuring T cells specific for a pool of CS peptides contained within the R21 vaccine by IFN-γ spleen ELISpot. The antibody response to the HBsAg was also assessed in an ELISA.

Anti-NANP Antibody ELISA ("NANP" Disclosed as SEQ ID NO: 7)

Anti-CSP antibodies induced by R21 immunisation were assessed in an ELISA using $NANP_6C$ peptide (SEQ ID NO: 12). The $NANP_6C$ peptide (SEQ ID NO: 12) consists of 6 copies of the NANP repeat followed by a C. Maxisorb (SEQ ID NO: 12). 96 well plates (Nunc) were coated with this antigen and incubated with serum samples using a 3 fold serial dilution starting at a dilution of 1:1000. Mouse antibodies were detected with alkaline phosphatase conjugated anti-mouse IgG and pNPP (p-Nitrophenyl Phosphate, Disodium Salt) substrate and absorbance read at 405 nm. The results are expressed as endpoint titre which is defined as the dilution at which the OD of the sample is equal to background.

The R21 particle vaccine was found to be highly immunogenic in mice and there is a notable boost effect after each vaccination (FIG. 4). Furthermore, if R21 is administered with the adjuvant Abisco or AddaVax slightly higher antibody titres were induced as compared to R21 administered with Alhydrogel.

IFN-γ spleen ELISpot

T cells induced by immunisation with R21 were measured using IFN-γ ELISpot assay. Fresh splenocytes were isolated and incubated in duplicate wells for 20 hours. Cells were restimulated with a pool of CS peptides spanning the entire CS protein at a final concentration of 2 ug/ml. Plates were coated and INF-γ was detected using antibodies from Mabtech. Spots were developed using an alkaline phosphatase substrate kit from Biorad and counted using an ELISPOT counter (AID). The results are presented in FIG. 6 and are expressed as number of spot forming cells (SFC) per million splenocytes.

T cell responses were only measured after the third vaccination. R21 administered with Abisco is more effective at inducing T cells to the CS peptides in mice than R21 administered with Ahydrogel.

Anti-HBsAg Antibody ELISA

Anti-HBsAg antibodies induced by R21 immunisation with Abisco adjuvant were assessed in an ELISA using HBsAg particle. The HBsAg particle was coated onto maxisorb 96 well plates (Nunc) and the plates were incubated with serum samples using a 3 fold serial dilution starting at a dilution of 1:100. Mouse IgG antibodies were detected and the results expressed as for the anti-NANP antibody ELISA ("NANP" disclosed as SEQ ID NO: 7) above.

HBsAg antibodies were assessed after three immunisations. Low antibody titres to the HBsAg were detected in all of the immunised mice in contrast to high titre antibodies against NANP (SEQ ID NO: 7; FIG. 5). This result shows that the R21 particle induces preferentially antibodies to the malaria rather than the hepatitis B component of R21.

Further experimentation supported the finding discussed above and in particular demonstrated that R21, when administered alone, is able to induce moderate CS-specific antibodies and T cells after 3 low dose immunisation. More specifically, groups of BALB/c mice were immunised intramuscularly with R21 alone or formulated with adjuvant as detailed in FIG. 11. Three immunisations were given three weeks apart and the immunogenicity was assessed by measuring serum antibody titres 3 weeks after each immunisation and antigen-specific T cell responses in the spleen 3 weeks after the final immunisation. After the third immunisation the CS-specific IgG titres (FIG. 12) and CS-specific T cells (FIG. 13) were not different between the groups receiving R21 alone or R21+Alhydrogel. These results demonstrate that R21 is immunogenic alone, and in the absence of an adjuvant can stimulate cellular immunity, and can still induce low levels of CS-specific IFN-γ producing T cell on its own.

Immunogenicity of R21 Particles with Viral Vector Vaccines in Mice

The immunogenicity of mixtures of R21 plus adjuvant with adenoviral and MVA viral vectors expressing the ME TRAP antigen (O'Hara et al J Infect Dis 2012) were assessed in BALB/c mice as detailed in Table 1. No impairment of humoral (FIG. 7) or T cell immunogenicity (FIG. 8) was observed with the mixtures. This is an important result as it indicates that despite the potential negative impact of an adjuvant on the immunogenicity of viral vectored vaccines, no negative impact was observed. This is surprising as many other adjuvants other than the saponin and emulsion types adjuvants used in this work have been found to negatively impact on the immunogenicity of viral vectors. This observation has potential utility as it could allow these two types of malaria vaccine, R21 which targets sporozoites, and viral vectors encoding the TRAP antigen, which target the liver-stage of malaria, to be combined successfully.

In particular a combination of R21, or a similar RTS or RTS,S like particle, plus a saponin containing adjuvant such as Abisco, matrix M, QS21, AS01 or AS02, plus MVA encoding TRAP or ME TRAP were identified as a novel and particularly preferred vaccine combination for malaria. FIGS. 7 and 8 show that this combination allows both exceptionally high antibody titres (to CSP) and T cell responses to TRAP to be attained. As these are arguably the best characterised correlates of protective immunity to pre-erythrocytic malaria in humans the use of this combination vaccine for boosting malaria immunity should be particularly effective. It is emphasized that MVA is a vector that allows multiple antigens to be expressed so the MVA expressing TRAP in this mixture may also express another malaria antigens, such as for example CSP, from the same or another MVA locus, or may even express an antigen from another pathogen, such as antigen 85A from *Mycobacterium tuberculosis*. This combination vaccine with an MVA expressing antigens from *Mycobacterium tuberculosis* as well as *Plasmodium falciparum*, along with R21 (or a similar particle such as RTS or RTS,S) plus a saponin adjuvant (such as matrix M or Iscomatrix or AS01 or AS02) or an emulsion adjuvant, such as Addavax or MF59, could therefore boost immunity to both tuberculosis and malaria.

TABLE 1

Vaccine co-administration study
Vaccine regimens used to assess the immunogenicity of R21 + adjuvant or ChAd63 ME TRAP - MVA ME TRAP in BALB/c mice administered alone or in combination. Combination vaccines formulated together and administered in the same syringe.

| Gp | No. mice | Particle + Adjuvant | No. shots | Viral vector | Interval |
|---|---|---|---|---|---|
| 1 | 6 | 0.5 µg R21 + Abisco IM | 2 | — | 8 weeks |
| 2 | 6 | — | — | 1 × 10^8 ChAd63 ME TRAP IM<br>1 × 10^6 MVA ME TRAP IM | 8 weeks |
| 3 | 6 | 0.5 µg R21 + Abisco IM | 2 | 1 × 10^8 ChAd63 ME TRAP IM<br>1 × 10^6 MVA ME TRAP IM | 8 weeks |

Immunogenicity of Viral Vector Insert with Adjuvants

On mixing R21 plus two adjuvants with the same adenoviral and MVA viral vectors an increased antibody response to the encoded antigen, TRAP, was surprisingly observed (FIG. 9). This was found whether or not the R21 particle was included in the mixture, indicating that both the saponin Abisco and the squalene-based emulsion Addavax can enhance antibody responses to a viral vector encoded insert. A variety of similar adjuvants such as QS21 formulations (like Abisco) and MF59 (like Addavax) are available and so may be used to enhance antibody responses to a viral vector encoded antigen.

Anti-TRAP Antibody ELISA

Anti-TRAP antibodies induced by viral vector immunisation were assessed in an ELISA using TRAP recombinant protein. The TRAP protein was coated onto maxisorb 96 well plates (Nunc) and the plates were incubated with serum samples using a 3 fold serial dilution starting at a dilution of 1:100. Mouse IgG antibodies were detected and the results expressed as for the anti-NANP antibody ELISA ("NANP" disclosed as SEQ ID NO: 7) above.

R21 can be Administered in a Number of Regimens for Optimal Immunogenicity

Groups of BALB/c mice were immunised with 4 different regimens as described in FIG. 14 with R21+Abisco-100, CS-specific antibodies were measured 3 weeks after each immunisation and CS-specific T cells were measured 3 weeks after the final immunisation FIGS. 15 & 16 respectively. After the final immunisations there was no difference between any groups in the level of CS-specific antibodies or T cells. This indicates that high titres antibodies and moderate levels of T cells can be generated with multiple regimens so interval will not affect the level of antibodies induced when R21 is combined with viral vectors.

R21 is More Immunogenic than CSP Recombinant Protein

Immunisation with R21 in a range of adjuvants induces higher antibody titres and CS-specific T cells than CSP recombinant protein. A study recently compared four CSP protein vaccines head to head to determine which elicited the highest immune responses and superior efficacy. The most immunogenic recombinant protein evaluated was produced in *E. coli* by Gennova (Pune, India) and this was obtained from PATH Malaria Vaccine Initiative (MVI, Washington D.C.) for assessment against R21. This assessment was performed with 3 different adjuvants Matrix M (similar to Abisco-100), MF59 (similar to AddaVax) and a biosimilar of the proprietary GSK adjuvant AS01, obtained from Lausanne here called L-AS01.

Groups of BALB/c mice were immunised twice, 8 weeks apart with 0.5 ug or either R21 or CSP formulated with 3 different adjuvants as detailed in FIG. 17. When comparing the two groups that received the same adjuvant, after prime the anti-NANP IgG ("NANP" disclosed as SEQ ID NO: 7) responses were higher in all groups receiving R21 compared to the groups receiving CSP, between, 2.6-4.7 fold higher (FIG. 18-A). The same trend was seen after boost at week 11, with the responses being between 4.5-22 fold greater in the R21 groups (FIG. 18-B). There was also no significant difference between the responses induced by the 3 adjuvants for either R21 or CSP, at any time point. Therefore if the data are pooled together for the R21 groups or the CSP groups at each time point the responses to the particle vaccine, R21 are significantly higher at all time-points than the recombinant protein in the 8 week prime boost regimen (FIG. 18-C). CS-specific T cell responses were also measured and mice immunised with the adjuvants Matrix M or L-AS01 adjuvants developed higher frequencies of T cells than those immunised with MF59 and those immunised with R21 induced higher frequencies of T cells than CSP (FIG. 19).

R21 is More Efficacious than CSP Recombinant Protein

R21 is not only more immunogenic but also more efficacious than CSP recombinant protein. Mice were immunised with R21 or CSP formulated with Matrix M and challenged with transgenic parasites (*P. berghei* transgenic for *P. falciparum* CSP) 3 weeks after boost. R21+Matrix M protected 87.5% of the vaccinated mice and CSP+Matrix M protected only 42.5% (FIG. 20-A). The levels of both CS-specific antibodies and T cells were also higher in the R21+Matrix M groups (FIG. 20-B+C).

Protective Efficacy of R21 Particles Against Malaria Sporozite Infection in a Mouse Model 34 Balb/c mice were divided into four groups. Group 1 was immunised with 0.5 micrograms of R21 in Abisco adjuvant intramuscularly, twice with an eight-week interval. Group 2 received the same dose of R21 with the very similar matrix M adjuvant (also supplied by Isconova, Uppsala, Sweden) with the same interval; the Matrix M is suitable for clinical use. Group 3 received a single dose of $1 \times 10^8$ ifu of a chimpanzee adenovirus (ChAd63) expressing the CS gene followed 8 weeks later by a single dose of $1 \times 10^6$ pfu of an MVA vector expressing the CS gene, both by the intramuscular route. Group 4 were immunised with adjuvant only twice with an 8 week interval, 5 mice receiving Abisco and 5 receiving Matrix M. Three weeks after the day of the booster immunisation all mice were infected by a 1000 sporozoites intravenously of a *P. berghei* parasite transgenic for the circumsporozoite gene of *P. falciparum*. Mice were scored for time to 1% parasitaemia by microscopy. 10/10 control adjuvant only mice were infected; 6/8 from Group 3 were infected showing modest efficacy with the vectored vaccines. In contrast only 1/16 mice in Groups 1 and 2 were infected showing 94% sterile efficacy with R21 with the ISCOM adjuvant formulations.

Vaccine Efficacy is Enhanced by Combining R21 and Viral Vectors

Immunisation with either R21+MF59 or the ChAd63 PbTRAP-MVA PbTRAP regimen was protective against sporozoite challenge in BALB/c mice eliciting a significant delay in the time taken to develop 1% parasitemia in the blood (FIGS. 21-A and B). Combining these two vaccine regimens together resulted in an increase in the efficacy of both vaccine regimens (FIGS. 21-C and D).

Vaccine Efficacy is Enhanced by Combining R21 and Viral Vectors

Groups of mice receiving a passive transfer of increasing doses of total IgG from mice immunised with R21+Matrix M were protected against sporozoite challenge in a dose dependant manner (FIG. 22). NANP-specific IgG ("NANP" disclosed as SEQ ID NO: 7) titres were measured 1 day after challenge (FIG. 23-A) and mice had good to moderate titres that correlated with the efficacy measured as delay to 1% parasitemia (FIG. 23-B).

The invention claimed is:

1. A virus-like particle comprising a fusion protein, wherein the fusion protein comprises at least one NANP repeat (SEQ ID NO: 7), and the C-terminus of the CS protein from *Plasmodium falciparum* comprising the sequence :

```
                                                 (SEQ ID NO: 6)
NKNNQGNGQGHNMPNDPNRNVDENANANSAVKNNNNEEPSDKIEKEYLN

KIQNSLSTEWSPCSVTCGNGIQVRIKPGSANKPKDELDYANDIEKKICK

MEKCSSVFN VVNSSIGI;
or the sequence
                                                 (SEQ ID NO: 4)
NKNNQGNGQGHNMPNDPNRNVDENANANSAVKNNNNEEPSDKHIKEYLN

KIQNSLSTEWSPCSVTCGNGIQVRIKPGSANKPKDELDYANDIEKKICK

MEKCSSV,
``` or a conservative substitution variant of SEQ ID No: 6 or SEQ ID NO: 4 with 95% or more sequence identity therewith; and HBsAg, wherein the virus-like particle comprises no free HBsAg.

2. The virus-like particle of claim 1 comprising at least 10 NANP repeats (SEQ ID NO: 13).

3. The virus-like particle of claim 1, wherein the particle comprises at least about 40% or more by mass of its proteinaceous material, the proteinaceous material being derived from *Plasmodium falciparum*.

4. The virus-like particle of claim 1 comprising a fusion protein consisting of:
the sequence of SEQ ID NO: 1 (R21);
the sequence of SEQ ID NO: 2 (RTS); or
a sequence with at least 95%, or more sequence identity with the sequence of SEQ ID NO: 1 or SEQ ID NO: 2.

5. A fusion protein comprising at least one NANP repeat (SEQ ID NO: 7), and the C terminus of the CS protein from *Plasmodium falciparum* comprising the sequence :

```
                                                 (SEQ ID NO: 6)
NKNNQGNGQGHNMPNDPNRNVDENANANSAVKNNNNEEPSDKIEKEYLN

KIQNSLSTEWSPCSVTCGNGIQVRIKPGSANKPKDELDYANDIEKKICK

MEKCSSVFN VVNSSIGI;
or the sequence
                                                 (SEQ ID NO: 4)
NKNNQGNGQGHNMPNDPNRNVDENANANSAVKNNNNEEPSDKHIKEYLN

KIQNSLSTEWSPCSVTCGNGIQVRIKPGSANKPKDELDYANDIEKKICK

MEKCSSV;
``` or a conservative substitution variant of SEQ ID No: 6 or SEQ ID NO: 4 sequence with 95% or more sequence identity therewith; and HBsAg, wherein the fusion protein comprises no free HBsAg.

6. The fusion protein of claim 5, wherein the fusion protein consists of, a sequence of SEQ ID NO: 1 (R21) or a sequence with at least 95% or more sequence identity with the sequence of SEQ ID NO: 1.

7. The fusion protein of claim 5, wherein the fusion protein is expressed in a *Saccharomyces cerevisiae* or *Pichia pastoris* or a methylotrophic yeast cell.

8. The fusion protein of claim 7, wherein the methylotrophic yeast cell is *Hansenula polymoipha*.

* * * * *

SEQUENCE LISTING

<160> NUMBER OF SEQ ID NOS: 13

<210> SEQ ID NO 1
<211> LENGTH: 410
<212> TYPE: PRT
<213> ORGANISM: Plasmodium falciparum

<400> SEQUENCE: 1

Met Asp Pro Asn Ala Asn Pro Asn Ala Asn Pro Asn Ala Asn Pro Asn
1               5                   10                  15

Ala Asn Pro Asn Ala Asn Pro Asn Ala Asn Pro Asn
                20                  25                  30

Ala Asn Pro Asn Ala Asn Pro Asn Ala Asn Pro Asn
        35                  40                  45

Ala Asn Pro Asn Ala Asn Pro Asn Ala Asn Pro Asn
    50                  55                  60

Ala Asn Pro Asn Ala Asn Pro Asn Lys Asn Gln
65                  70                  75              80

Gly Asn Gly Gln Gly His Asn Met Pro Asn Asp Pro Asn Arg Asn Val
                85                  90                  95

Asp Glu Asn Ala Asn Ala Asn Ser Ala Val Lys Asn Asn Asn Glu
            100                 105                 110

Glu Pro Ser Asp Lys His Ile Lys Glu Tyr Leu Asn Lys Ile Gln Asn
            115                 120                 125

Ser Leu Ser Thr Glu Trp Ser Pro Cys Ser Val Thr Cys Gly Asn Gly
        130                 135                 140

Ile Gln Val Arg Ile Lys Pro Gly Ser Ala Asn Lys Pro Lys Asp Glu
145                 150                 155                 160

Leu Asp Tyr Ala Asn Asp Ile Glu Lys Lys Ile Cys Lys Met Glu Lys
                165                 170                 175

Cys Ser Ser Val Pro Val Thr Asn Met Glu Asn Ile Thr Ser Gly Phe
            180                 185                 190

Leu Gly Pro Leu Leu Val Leu Gln Ala Gly Phe Phe Leu Leu Thr Arg
        195                 200                 205

Ile Leu Thr Ile Pro Gln Ser Leu Asp Ser Trp Trp Thr Ser Leu Asn
210                 215                 220

Phe Leu Gly Gly Ser Pro Val Cys Leu Gly Gln Asn Ser Gln Ser Pro
225                 230                 235                 240

Thr Ser Asn His Ser Pro Thr Ser Cys Pro Pro Ile Cys Pro Gly Tyr
                245                 250                 255

Arg Trp Met Cys Leu Arg Arg Phe Ile Ile Phe Leu Phe Ile Leu Leu
            260                 265                 270

Leu Cys Leu Ile Phe Leu Leu Val Leu Leu Asp Tyr Gln Gly Met Leu
        275                 280                 285

Pro Val Cys Pro Leu Ile Pro Gly Ser Thr Thr Thr Asn Thr Gly Pro
290                 295                 300

Cys Lys Thr Cys Thr Thr Pro Ala Gln Gly Asn Ser Met Phe Pro Ser
305                 310                 315                 320

Cys Cys Cys Thr Lys Pro Thr Asp Gly Asn Cys Thr Cys Ile Pro Ile
                325                 330                 335

Pro Ser Ser Trp Ala Phe Ala Lys Tyr Leu Trp Glu Trp Ala Ser Val
            340                 345                 350

Arg Phe Ser Trp Leu Ser Leu Leu Val Pro Phe Val Gln Trp Phe Val
        355                 360                 365

Gly Leu Ser Pro Thr Val Trp Leu Ser Ala Ile Trp Met Met Trp Tyr
            370                 375                 380

Trp Gly Pro Ser Leu Tyr Ser Ile Val Ser Pro Phe Ile Pro Leu Leu
385                 390                 395                 400

Pro Ile Phe Phe Cys Leu Trp Val Tyr Ile
                405                 410

<210> SEQ ID NO 2
<211> LENGTH: 424

<212> TYPE: PRT
<213> ORGANISM: Plasmodium falciparum

<400> SEQUENCE: 2

Met Met Ala Pro Asp Pro Asn Ala Asn Pro Asn Ala Asn Pro Asn Ala
1               5                   10                  15

Asn Pro Asn Ala Asn Pro Asn Ala Asn Pro Asn Ala Asn Pro Asn Ala
            20                  25                  30

Asn Pro Asn Ala Asn Pro Asn Ala Asn Pro Asn Ala Asn Pro Asn Ala
        35                  40                  45

Asn Pro Asn Ala Asn Pro Asn Ala Asn Pro Asn Ala Asn Pro Asn Ala
    50                  55                  60

Asn Pro Asn Ala Asn Pro Asn Ala Asn Pro Asn Ala Asn Pro Asn Lys
65                  70                  75                  80

Asn Asn Gln Gly Asn Gly Gln Gly His Asn Met Pro Asn Asp Pro Asn
                85                  90                  95

Arg Asn Val Asp Glu Asn Ala Asn Ala Asn Ser Ala Val Lys Asn Asn
            100                 105                 110

Asn Asn Glu Glu Pro Ser Asp Lys His Ile Lys Glu Tyr Leu Asn Lys
        115                 120                 125

Ile Gln Asn Ser Leu Ser Thr Glu Trp Ser Pro Cys Ser Val Thr Cys
    130                 135                 140

Gly Asn Gly Ile Gln Val Arg Ile Lys Pro Gly Ser Ala Asn Lys Pro
145                 150                 155                 160

Lys Asp Glu Leu Asp Tyr Ala Asn Asp Ile Glu Lys Lys Ile Cys Lys
                165                 170                 175

Met Glu Lys Cys Ser Ser Val Phe Asn Val Val Asn Ser Ser Ile Gly
            180                 185                 190

Leu Gly Pro Val Thr Asn Met Glu Asn Ile Thr Ser Gly Phe Leu Gly
        195                 200                 205

Pro Leu Leu Val Leu Gln Ala Gly Phe Phe Leu Leu Thr Arg Ile Leu
    210                 215                 220

Thr Ile Pro Gln Ser Leu Asp Ser Trp Trp Thr Ser Leu Asn Phe Leu
225                 230                 235                 240

Gly Gly Ser Pro Val Cys Leu Gly Gln Asn Ser Gln Ser Pro Thr Ser
                245                 250                 255

Asn His Ser Pro Thr Ser Cys Pro Pro Ile Cys Pro Gly Tyr Arg Trp
            260                 265                 270

Met Cys Leu Arg Arg Phe Ile Ile Phe Leu Phe Ile Leu Leu Leu Cys
        275                 280                 285

Leu Ile Phe Leu Leu Val Leu Leu Asp Tyr Gln Gly Met Leu Pro Val
    290                 295                 300

Cys Pro Leu Ile Pro Gly Ser Thr Thr Thr Asn Thr Gly Pro Cys Lys
305                 310                 315                 320

Thr Cys Thr Thr Pro Ala Gln Gly Asn Ser Met Phe Pro Ser Cys Cys
                325                 330                 335

Cys Thr Lys Pro Thr Asp Gly Asn Cys Thr Cys Ile Pro Ile Pro Ser
            340                 345                 350

Ser Trp Ala Phe Ala Lys Tyr Leu Trp Glu Trp Ala Ser Val Arg Phe
        355                 360                 365

Ser Trp Leu Ser Leu Leu Val Pro Phe Val Gln Trp Phe Val Gly Leu
    370                 375                 380

Ser Pro Thr Val Trp Leu Ser Ala Ile Trp Met Met Trp Tyr Trp Gly
385                 390                 395                 400

```
Pro Ser Leu Tyr Ser Ile Val Ser Pro Phe Ile Pro Leu Leu Pro Ile
            405                 410                 415

Phe Phe Cys Leu Trp Val Tyr Ile
            420

<210> SEQ ID NO 3
<211> LENGTH: 75
<212> TYPE: PRT
<213> ORGANISM: Plasmodium falciparum

<400> SEQUENCE: 3

Met Asp Pro Asn Ala Asn Pro Asn Ala Asn Pro Asn Ala Asn Pro Asn
1               5                   10                  15

Ala Asn Pro Asn Ala Asn Pro Asn Ala Asn Pro Asn Ala Asn Pro Asn
            20                  25                  30

Ala Asn Pro Asn Ala Asn Pro Asn Ala Asn Pro Asn Ala Asn Pro Asn
        35                  40                  45

Ala Asn Pro Asn Ala Asn Pro Asn Ala Asn Pro Asn Ala Asn Pro Asn
    50                  55                  60

Ala Asn Pro Asn Ala Asn Pro Asn Ala Asn Pro
65                  70                  75

<210> SEQ ID NO 4
<211> LENGTH: 105
<212> TYPE: PRT
<213> ORGANISM: Plasmodium falciparum

<400> SEQUENCE: 4

Asn Lys Asn Asn Gln Gly Asn Gly Gln Gly His Asn Met Pro Asn Asp
1               5                   10                  15

Pro Asn Arg Asn Val Asp Glu Asn Ala Asn Ala Asn Ser Ala Val Lys
            20                  25                  30

Asn Asn Asn Asn Glu Glu Pro Ser Asp Lys His Ile Lys Glu Tyr Leu
        35                  40                  45

Asn Lys Ile Gln Asn Ser Leu Ser Thr Glu Trp Ser Pro Cys Ser Val
    50                  55                  60

Thr Cys Gly Asn Gly Ile Gln Val Arg Ile Lys Pro Gly Ser Ala Asn
65                  70                  75                  80

Lys Pro Lys Asp Glu Leu Asp Tyr Ala Asn Asp Ile Glu Lys Lys Ile
                85                  90                  95

Cys Lys Met Glu Lys Cys Ser Ser Val
            100                 105

<210> SEQ ID NO 5
<211> LENGTH: 226
<212> TYPE: PRT
<213> ORGANISM: Hepatitis B virus

<400> SEQUENCE: 5

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60
```

```
Cys Pro Pro Ile Cys Pro Gly Tyr Arg Trp Met Cys Leu Arg Arg Phe
 65                  70                  75                  80

Ile Ile Phe Leu Phe Ile Leu Leu Cys Leu Ile Phe Leu Leu Val
                 85                  90                  95

Leu Leu Asp Tyr Gln Gly Met Leu Pro Val Cys Pro Leu Ile Pro Gly
            100                 105                 110

Ser Thr Thr Thr Asn Thr Gly Pro Cys Lys Thr Cys Thr Thr Pro Ala
            115                 120                 125

Gln Gly Asn Ser Met Phe Pro Ser Cys Cys Thr Lys Pro Thr Asp
        130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
            195                 200                 205

Val Ser Pro Phe Ile Pro Leu Leu Pro Ile Phe Phe Cys Leu Trp Val
210                 215                 220

Tyr Ile
225

<210> SEQ ID NO 6
<211> LENGTH: 115
<212> TYPE: PRT
<213> ORGANISM: Plasmodium falciparum

<400> SEQUENCE: 6

Asn Lys Asn Asn Gln Gly Asn Gly Gln Gly His Asn Met Pro Asn Asp
  1               5                  10                  15

Pro Asn Arg Asn Val Asp Glu Asn Ala Asn Ala Asn Ser Ala Val Lys
             20                  25                  30

Asn Asn Asn Asn Glu Glu Pro Ser Asp Lys His Ile Lys Glu Tyr Leu
         35                  40                  45

Asn Lys Ile Gln Asn Ser Leu Ser Thr Glu Trp Ser Pro Cys Ser Val
     50                  55                  60

Thr Cys Gly Asn Gly Ile Gln Val Arg Ile Lys Pro Gly Ser Ala Asn
 65                  70                  75                  80

Lys Pro Lys Asp Glu Leu Asp Tyr Ala Asn Asp Ile Glu Lys Lys Ile
                 85                  90                  95

Cys Lys Met Glu Lys Cys Ser Ser Val Phe Asn Val Val Asn Ser Ser
            100                 105                 110

Ile Gly Ile
        115

<210> SEQ ID NO 7
<211> LENGTH: 4
<212> TYPE: PRT
<213> ORGANISM: Plasmodium falciparum

<400> SEQUENCE: 7

Asn Ala Asn Pro
  1

<210> SEQ ID NO 8
<211> LENGTH: 72
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(72)
<223> OTHER INFORMATION: This sequence may encompass 1-18 "Asn Ala Asn
      Pro" repeats; See specification as filed for detailed description
      of preferred embodiments

<400> SEQUENCE: 8

Asn Ala Asn Pro Asn Ala Asn Pro Asn Ala Asn Pro Asn Ala Asn Pro
1               5                   10                  15

Asn Ala Asn Pro Asn Ala Asn Pro Asn Ala Asn Pro Asn Ala Asn Pro
            20                  25                  30

Asn Ala Asn Pro Asn Ala Asn Pro Asn Ala Asn Pro Asn Ala Asn Pro
        35                  40                  45

Asn Ala Asn Pro Asn Ala Asn Pro Asn Ala Asn Pro Asn Ala Asn Pro
    50                  55                  60

Asn Ala Asn Pro Asn Ala Asn Pro
65                  70

<210> SEQ ID NO 9
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asn Ala Asn Pro Asn Ala Asn Pro Asn Ala Asn Pro Asn Ala Asn Pro
1               5                   10                  15

Asn Ala Asn Pro Asn Ala Asn Pro Asn Ala Asn Pro Asn Ala Asn Pro
            20                  25                  30

Asn Ala Asn Pro Asn Ala Asn Pro Asn Ala Asn Pro Asn Ala Asn Pro
        35                  40                  45

Asn Ala Asn Pro Asn Ala Asn Pro Asn Ala Asn Pro Asn Ala Asn Pro
    50                  55                  60

Asn Ala Asn Pro Asn Ala Asn Pro
65                  70

<210> SEQ ID NO 10
<211> LENGTH: 10
<212> TYPE: PRT
<213> ORGANISM: Plasmodium falciparum

<400> SEQUENCE: 10

Phe Asn Val Val Asn Ser Ser Ile Gly Leu
1               5                   10

<210> SEQ ID NO 11
<211> LENGTH: 4
<212> TYPE: PRT
<213> ORGANISM: Hepatitis B virus

<400> SEQUENCE: 11

Pro Val Thr Asn
1

<210> SEQ ID NO 12
```

```
<211> LENGTH: 25
<212> TYPE: PRT
<213> ORGANISM: Plasmodium falciparum

<400> SEQUENCE: 12

Asn Ala Asn Pro Asn Ala Asn Pro Asn Ala Asn Pro Asn Ala Asn Pro
1               5                   10                  15

Asn Ala Asn Pro Asn Ala Asn Pro Cys
            20                  25

<210> SEQ ID NO 13
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asn Ala Asn Pro Asn Ala Asn Pro Asn Ala Asn Pro Asn Ala Asn Pro
1               5                   10                  15

Asn Ala Asn Pro Asn Ala Asn Pro Asn Ala Asn Pro Asn Ala Asn Pro
            20                  25                  30

Asn Ala Asn Pro Asn Ala Asn Pro
            35                  40
```